US009918866B2

(12) United States Patent
Summit et al.

(10) Patent No.: US 9,918,866 B2
(45) Date of Patent: *Mar. 20, 2018

(54) BIKINI BRACE

(71) Applicant: 3D Systems, Inc., Rock Hill, SC (US)

(72) Inventors: Scott Summit, Mill Valley, CA (US); Kenneth B Trauner, San Francisco, CA (US)

(73) Assignee: 3D SYSTEMS, INC., Rock Hill, SC (US)

( * ) Notice: Subject to any disclaimer, the term of this patent is extended or adjusted under 35 U.S.C. 154(b) by 372 days.

This patent is subject to a terminal disclaimer.

(21) Appl. No.: 13/791,708

(22) Filed: Mar. 8, 2013

(65) Prior Publication Data

US 2014/0142486 A1 May 22, 2014

Related U.S. Application Data

(63) Continuation-in-part of application No. PCT/US2012/051612, filed on Aug. 20, 2012, which is a continuation-in-part of application No. 13/214,096, filed on Aug. 19, 2011, now abandoned, which is a continuation-in-part of application No. 12/820,968, filed on Jun. 22, 2010, now abandoned, which is a continuation-in-part of application No. 12/615,196, filed on Nov. 9, 2009, now Pat. No. 8,005,651.

(60) Provisional application No. 61/720,878, filed on Oct. 31, 2012, provisional application No. 61/112,751, filed on Nov. 9, 2008, provisional application No.

(Continued)

(51) Int. Cl.
*A61F 5/05* (2006.01)
*A61F 5/058* (2006.01)
*A61F 5/01* (2006.01)

(52) U.S. Cl.
CPC ........ *A61F 5/05841* (2013.01); *A61F 5/0104* (2013.01)

(58) Field of Classification Search
CPC A61F 5/05866; A61F 5/05858; A61F 5/0118; A61F 5/01; A61F 5/013
USPC .................................... 602/6–7, 21
See application file for complete search history.

(56) References Cited

U.S. PATENT DOCUMENTS 3,529,601 A  9/1970 Kirkland
4,854,310 A * 8/1989 Lee ..................... A61F 5/05866
                                                           602/21

(Continued)

FOREIGN PATENT DOCUMENTS

JP      3040335     5/1997
JP   2003-522594    4/2012

(Continued)

OTHER PUBLICATIONS

PCT International Search Report for International Application No. PCT/US13/66956, dated Jan. 17, 2014 (3 pages).

(Continued)

*Primary Examiner* — Kari Rodriquez
(74) *Attorney, Agent, or Firm* — Staniford Tomita LLP

(57) ABSTRACT

A bikini brace has an inner surface that corresponds to a digital representation of an injured limb. The bikini brace can wrap around a length of the limb in a helical manner. The body of the bikini brace may be a single piece structure that is fenestrated to provide air circulation to the injured limb.

19 Claims, 19 Drawing Sheets

Related U.S. Application Data

61/168,183, filed on Apr. 9, 2009, provisional application No. 61/185,781, filed on Jun. 10, 2009.

(56) References Cited

U.S. PATENT DOCUMENTS

| | | | |
|---|---|---|---|
| 5,279,545 A * | 1/1994 | Reese, Sr. | A61F 5/013 602/21 |
| 5,836,902 A * | 11/1998 | Gray | A61F 5/0111 128/882 |
| 6,142,965 A | 11/2000 | Mathewson | |
| 6,267,743 B1 | 7/2001 | Bodenschatz et al. | |
| 6,783,507 B1 | 8/2004 | Fisher | |
| 6,942,628 B1 * | 9/2005 | Watson | A61F 13/04 602/6 |
| 7,797,072 B2 | 9/2010 | Summit | |
| 7,867,192 B2 | 1/2011 | Iglesias et al. | |
| 2004/0121683 A1 | 6/2004 | Jordan et al. | |
| 2005/0267391 A1 * | 12/2005 | Garelick | A61F 5/0118 602/21 |
| 2005/0288809 A1 | 12/2005 | Spaeth et al. | |
| 2006/0069335 A1 * | 3/2006 | Fritsch | A61F 5/0118 602/5 |
| 2007/0016323 A1 | 1/2007 | Fried | |
| 2010/0138193 A1 * | 6/2010 | Summit | G06F 17/50 703/1 |
| 2010/0262054 A1 | 10/2010 | Summit et al. | |
| 2010/0298750 A1 | 11/2010 | Chiang et al. | |
| 2011/0301520 A1 | 12/2011 | Summit et al. | |
| 2014/0052039 A1 * | 2/2014 | Summit et al. | 602/21 |

FOREIGN PATENT DOCUMENTS

| | | |
|---|---|---|
| JP | 2012-508075 | 4/2012 |
| JP | 2005-279153 | 10/2013 |
| WO | 2011031971 | 3/2011 |
| WO | 2012018785 | 2/2012 |

OTHER PUBLICATIONS

PCT Written Opinion of the International Searching Authority for International Application No. PCT/US13/66956, dated Jan. 17, 2014 (6 pages).
English Translation of Japan's First Office Action for Japanese Patent Application No. 2015-540717, dated Jun. 28, 2016 (9 pages).
Extended European Search Report for European Patent Application No. EP13850662.1 dated Jun. 8, 2016 (7 pages).
English Translation of Japan's Decision of Rejection for Japanese Patent Application No. 2015-540717, dated Feb. 21, 2017 (3 pages).

* cited by examiner

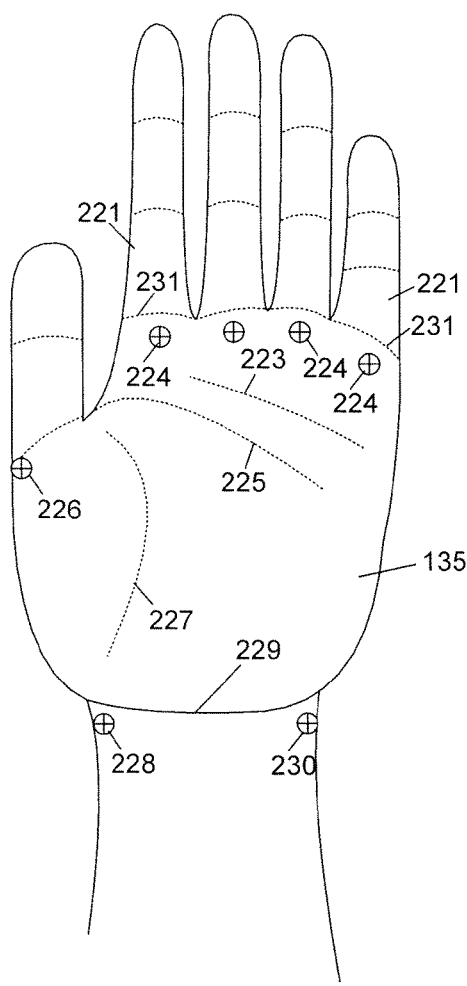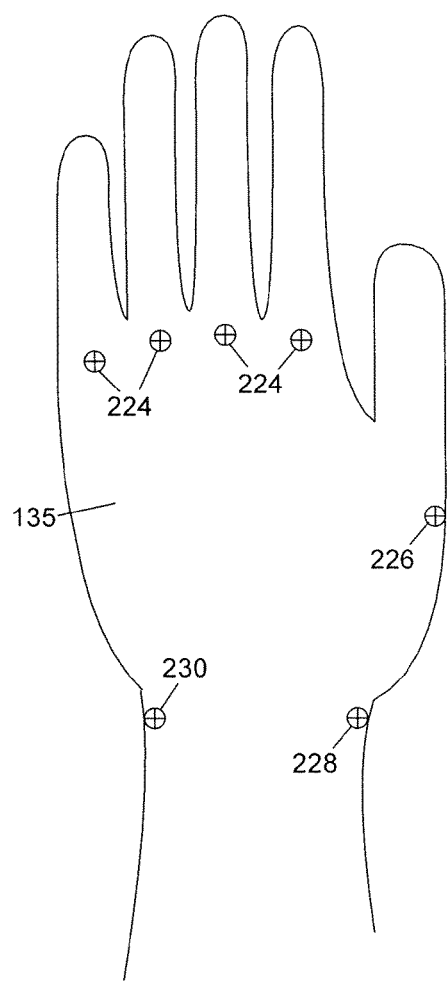
FIG. 17
FIG. 18

BIKINI BRACE

CROSS REFERENCE TO RELATED APPLICATIONS

This application claims priority to U.S. Provisional Application No. 61/720,878, "Bikini Brace" filed Oct. 31, 2012 and is a continuation-in-part of PCT Patent Application No. PCT/US2012/051612, "Adjustable Brace" filed Aug. 20, 2012 which claims priority to U.S. patent application Ser. No. 13/214,096, "Adjustable Brace" filed Aug. 19, 2011 which is a continuation-in-part of U.S. patent application Ser. No. 12/820,968, "Modular Custom Braces, Casts And Devices And Methods For Designing And Fabricating filed Jun. 22, 2010 which is a continuation-in-part of U.S. patent application Ser. No. 12/615,196, now U.S. Pat. No. 8,005,651, "Custom Braces, Casts and Devices And Methods For Designing And Fabricating" filed Nov. 9, 2009 which claims priority to U.S. Provisional Patent Application No. 61/112,751, "Brace And Cast" filed on Nov. 9, 2008, U.S. Provisional Patent Application No. 61/168,183, "Orthopedic Braces" filed in Apr. 9, 2009, and U.S. Provisional Patent Application No. 61/185,781, "Bespoke Fracture Brace" filed in Jun. 10, 2009. The contents of PCT Application No. PCT/US2012/051612 and U.S. Patent Application Nos. 61/720,878, 13/214,096, 12/820,968, 12/615,196, 61/375,699, 61/112,751, 61/168,183, and 61/185,781 are hereby incorporated by reference.

BACKGROUND

A problem with braces is that they can be complicated to secure to the patient's body, uncomfortable to wear and unattractive to look at. Many braces have thick padding that is secured around the injured limb and a rigid structure that prevents the brace from moving which immobilizes the limb. Because of these issues, many patients tend to not wear braces that have been fitted to the patients by their physicians. What is needed is an improved and simplified brace that is easily placed on the patient's body, comfortable to wear and more attractive than existing braces.

SUMMARY OF THE INVENTION

The present invention is directed towards a brace that can have a minimal structural configuration that is placed around an injured limb to prevent or restrict movement of the limb. For the purposes of describing a minimal structure that is similar to a bikini bathing suit, the brace is described in the application as a "bikini" brace and is intended to mean a brace having a minimal structural design. Thus, the bikini brace may only provide the required support or movement resistance at the designed locations rather than around the entire limb rather than providing a brace that completely surrounds most or all exposed areas of the injured limb. Because the bikini brace is designed to fit around an elongated limb, the brace can define a center axis. The bikini brace may also have holes or fenestrations to allow air to circulate around the portions of the limb covered by the bikini brace.

The bikini brace can have a distal portion, a middle portion and a proximal portion. In an embodiment, the distal portion of the bikini brace can be placed on the limb by inserting a portion of the limb in an opening in the distal portion of the bikini brace so that the limb occupies the center axis of the brace. Once the limb is properly positioned in the distal portion, the middle and proximal portions of the bikini brace can be placed over the limb. One or more fasteners may be used to secure the brace to the limb. The brace can allow axial twisting or rotation of the limb, but may prevent bending movements of the limb. For example, if the brace is an arm brace, it may allow rotation about a center axis of the brace relative to the forearm such as axial rotation of the hand for movements such as rotating door knobs. The brace may also prevent bending of the wrist such as palmar flexion movement of the hand.

There are various features that make the bikini brace comfortable to wear. The inner surface of the brace can correspond to a digital representation of the injured limb so that the brace will provide a custom fit for the patient's limb. Because the bikini brace is thin it can be easily worn under clothing. The brace is also light weight and fenestrated to allow the limb to be exposed to ambient air so that perspiration from the limb can evaporate rather than being trapped by the brace. A bikini brace can have thickness that is between about 0.05 inch and 0.50 inch. The width of the structural bikini brace sections can be between about 0.25 inch and 2 inches. Because the brace is thin and light weight, the patient is more likely to wear the inventive bikini brace.

In an embodiment, the bikini brace can be used as an arm brace. The brace can have a proximal portion that fits around a forearm portion of the limb and a distal portion of the brace body fits around a hand portion of the limb. The distal hand portion of the brace can have a lower section that supports a palm of the hand portion and an upper section that fits over a dorsum of the hand portion. Because the inner surfaces of the distal portion can correspond to a digital representation of the hand, there will be a very close fit that can keep the bikini brace in proper alignment with the arm. Because the surface of the palm of the hand is normally concave, the inner surface of the brace body at the lower section of the distal portion includes a convex surface that corresponds to the concave surface of the palm.

The bikini brace can also be configured to provide specific types of support for the hand. For example, in an embodiment, the distal limb support at the distal end of the brace may completely surround a portion of the hand and a distal edge of the brace can be adjacent to or cover some or all of the palmar digital creases of the hand. The distal edge of the bikini brace may also not extend over proximal phalanx segments of the fingers so that the movement of fingers may be restricted but not completely prevented. In an embodiment, the distal limb support of the brace does not extend over a thenar portion of the hand allowing a thumb of the hand to move freely. By knowing the type of hand injury, a distal portion of the bikini brace can be designed to prevent or restrict movement that can provide the best rehabilitation or therapy for the limb. The bikini brace can also be designed to allow other movement of the hand to improve comfort and allow as must hand mobility as possible.

If the brace is being used to prevent movement of the wrist to prevent carpal tunnel injury, the bikini brace can include structural members around the arm that will prevent wrist movement. For example, the bikini brace can include a distal limb support that is adjacent to a palmar surface of the hand, a middle section that includes a plurality of elongated beams that extend along the length of the brace and a proximal limb support that fully or partially surrounds a portion of the forearm. If the patient attempts to move the palm in a downward motion about the wrist, the downward force will be resisted by the middle section and the proximal section. Although the brace can allow some movement, the brace functions to resist wrist movement to prevent injuries such as median nerve entrapment or carpal tunnel syndrome.

In order to design a custom bikini brace, a digital representation of the injured limb may first be obtained through a plurality of photographs. One or more colored stickers can be applied to the patient's limb and a plurality of markings or points of visible or IR light can be projected to the patient's limb. The light sources can project a pattern of light spots onto the limb. The limb can be placed on a positioning stand between a plurality of infrared (IR) and/or visible light cameras. A doctor may mark the injured areas of the limb with a pen, stickers or any other suitable marker that provide a suitable contrast to the skin of the patient. Some of the markings can be used for position detection. Markings can also indicate the areas where the patient is injured such as bone breakage, or swollen areas, etc. Other markings can indicate desired an edge or a seam of the brace. These markings can be captured by the digital photographic images and the marking locations can be used to design the adjustable brace. From the photographs, a three dimensional digital representation of the limb can be created by photogrammetry, image correlation, depth mapping or any other suitable IR and/or visible light photography based surface topography detection method. From the three dimensional representation of the limb surface topography, a bikini brace can be designed having an inner surface that corresponds to the three dimensional digital representation of the patient's limb.

In an embodiment, the brace or cast has a smooth inner surface that conforms to the digital representation of the scanned surface of the limb and closely matches the surface measurements of the patient's body. Because the inner surface of the brace accurately conforms to the patient to provide a very close fit, the surface of the limb matches the inner surface of the brace and the brace can be worn by the patient without any padding. The brace can be made of a hard plastic material and the inner surface of the brace should also be very smooth. In order to be comfortable, the inner surface can have a surface finish of less than of less than 500 $R_a$ μ inch. A brace or cast that can be worn by a patient without padding has several benefits including: simplified brace design and construction, less weight, lower profile, better ventilation, no absorption of water, easier cleaning, etc.

The inventive custom design process is unique because it provides a virtual fitting of the brace to the patient prior to fabrication of the actual device. Because the innermost surfaces of the brace can be designed to be a very close fit to the patient, no additional padding may be needed. No other known system provides the ability to design custom adjustable braces in a virtual manner. In particular, the inventive process can detect marking placed on a body and utilize this information to design the adjustable brace based upon the location of the mark.

BRIEF DESCRIPTION OF THE DRAWINGS

FIGS. 17-18 illustrate dorsal and palmar views of a hand;

DETAILED DESCRIPTION

The present invention is a custom designed bikini brace having interior surfaces that corresponds closely to a digital representation of a portion of a patient's body which can be from an optical scan of the patient. When a patient injures a limb, the bikini brace can be designed to closely fit around the limb and resist specific types of movement. For example, a bikini brace can be an arm brace that allows movement of the fingers and thumb as well as axial rotation of the hand so that the patient can grasp items, type on a keyboard and rotate door knobs to open doors. However, the bikini brace can prevent the arm from bending of the wrist. This can be helpful in preventing injuries such as carpal tunnel syndrome.

Figure 1:
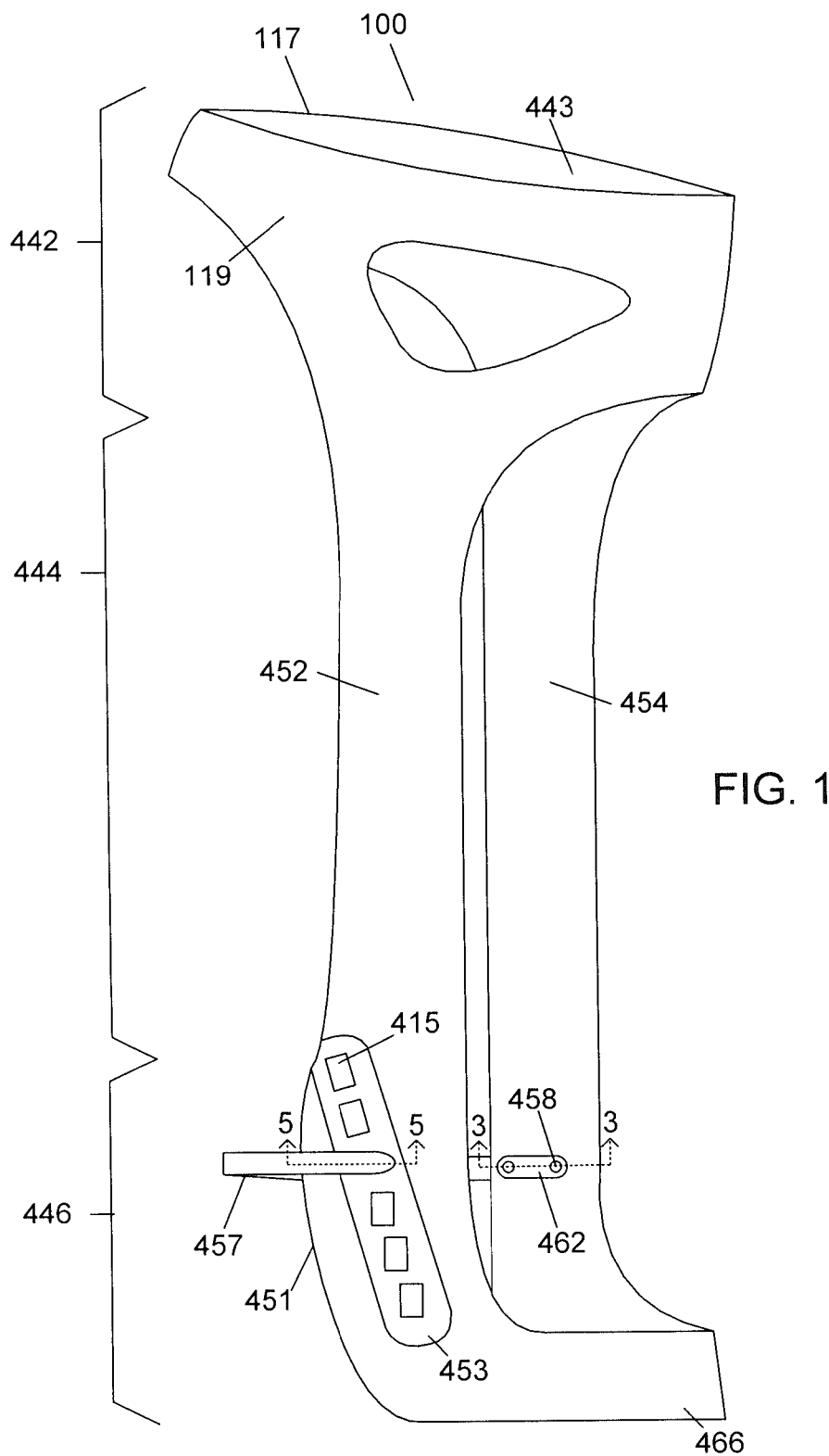
FIGS. 1-2 illustrate an embodiment of a bikini brace.
Figure 2:
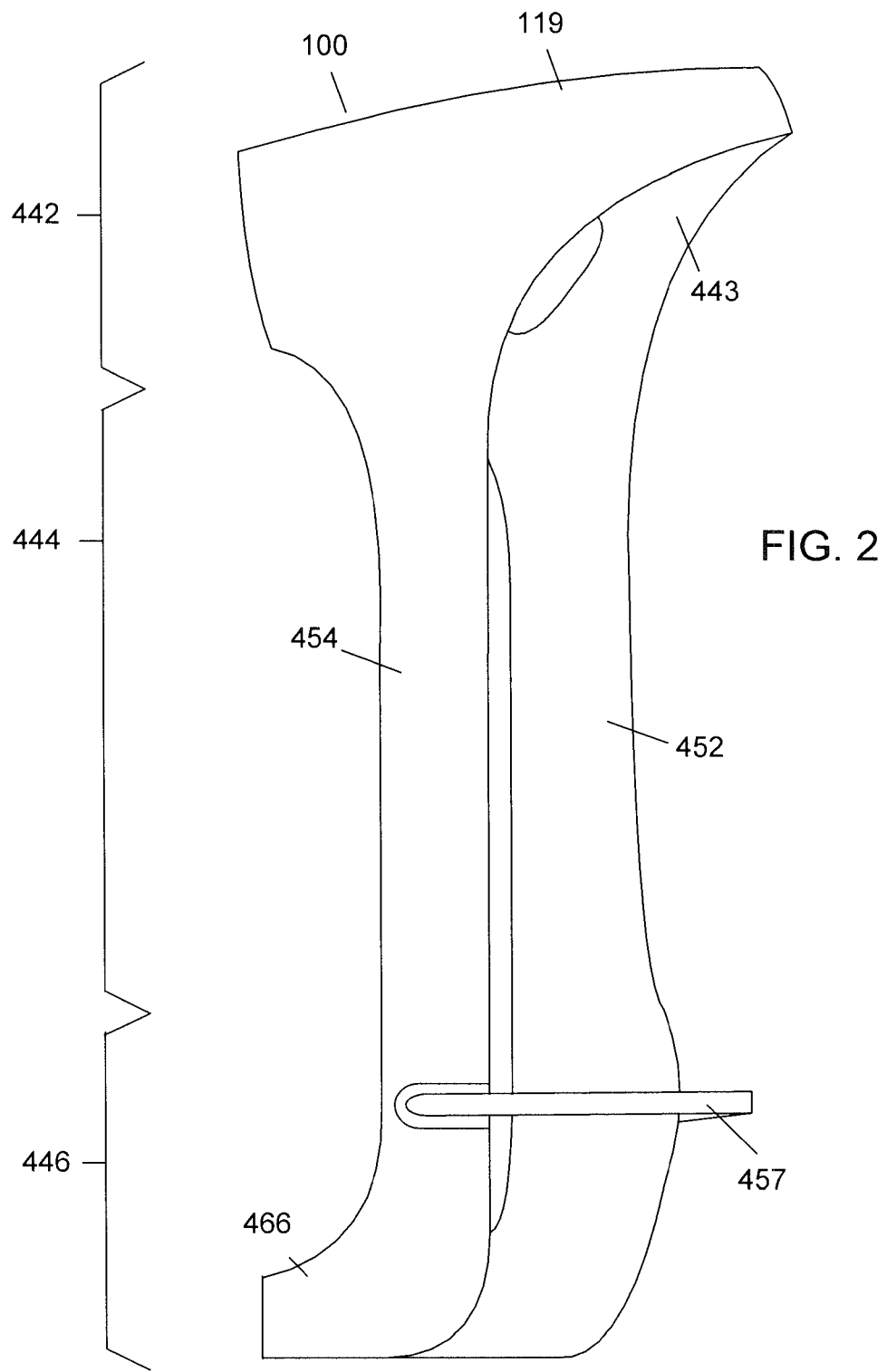

FIG. 1 illustrates a top view and FIG. 2 illustrates a bottom view of an embodiment of a bikini arm brace 100. The hand and forearm brace 100 can be used to prevent movement between the patient's arm and hand by holding the patient's wrist in a fixed predetermined position. The inner surface 443 of the brace 100 corresponds to a digital representation of the surface of the arm. Because the surface of the palm of the hand is normally concave, the inner surface 443 of the brace 100 at the lower section 117 of the distal portion 115 can include a convex surface that corresponds to the concave surface of the palm.

The brace 100 can have a distal hand portion 442 and a middle section 444 that includes an upper elongated portion 452 and a lower elongated portion 454 that extend along the length of the brace 100. The brace 100 can also include a proximal forearm portion 446. The upper elongated portion 452 and the lower elongated portion 454 can be connected to both the distal hand portion 442 and the proximal forearm portion 466 of the brace 100. The upper elongated portion 452 and the lower elongated portion 454 provide support and rigidity to prevent the hand portion 442 from moving relative to the forearm portion 444. The interior surfaces of the upper elongated portion 452, the lower elongated portion 454 and the end portion 466 can correspond to the digital representation of the patient forearm.

In the illustrated embodiment, the hand portion 442 has a fixed design and may not be adjustable. This non-adjustable hand section 442 can be useful if the brace does not need to be opened at the hand in order to be placed on the patient. The adjustability may not be important because the brace is a precise match to the digital representation of the patient's hand. In this embodiment, the patient can place the hand in the hand section 442 and then place the forearm between the upper elongated portion 452 and the lower elongated portion 454. The patient can then attach the adjustable member 457 around the forearm to secure the end portion 466 of the brace 100 against the forearm. Because the wrist is immobilized by the brace 100, the muscles in the forearm may decrease in size due to atrophy and the adjustable member 457 can be used to adjust the cross sectional area of the brace 100 to provide an optimum fit as the forearm cross section changes. The brace 100 can have a plurality of slots or holes 415 that are adjacent to each other and formed in a thicker portion 453 of the brace 100. The plurality of slots or holes 415 can each be positioned at a different distance from the edge 451 of the brace 100. The adjustable member 457 can be set to a larger size by placing the hook 419 into a hole 415 that is closer to the edge of the brace 100.

Figure 3:
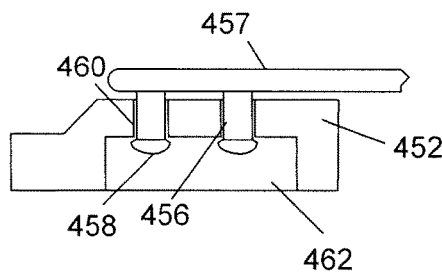
FIGS. 3-7 illustrate an embodiment of an adjustable member.

In an embodiment, the adjustable member 457 can be created as an integrated portion of the brace 100. For example, if the brace 100 is fabricated using a 3D printing machine, the adjustable member 457 is formed with the brace 100 as a single integrated structure. However, in other embodiments, the adjustable member 457 can be a separate component that is attached to the brace 100 but may not be an integrated part of the brace structure. FIG. 3 is a cross section view of a portion of an embodiment of the brace 100 illustrated if FIG. 1. In an embodiment, the adjustable member 457 can be a separate structure that includes one or more fastening pins 456 that have flared tips 458 and are placed through holes 460 in the brace 100. The diameter of the pins 456 can be smaller than the diameter of the holes 460 but the outer diameter of the tips 458 can be larger than the diameter of the holes 460. By pressing the flared tips 458 through the holes 460, the adjustable member 457 is secured to the brace 100. The brace 100 can have a recessed portion 462 so that the tips 458 are above the inner surface of the brace 100. This design also allows the adjustable member to be replaced if necessary. For example, the adjustable member 457 may break or a different length adjustable member can be used to provide a better fit on the patient. In an embodiment, the adjustable member can be stocked in various lengths and attached to the brace 100 after it has been fabricated.

Figure 4:
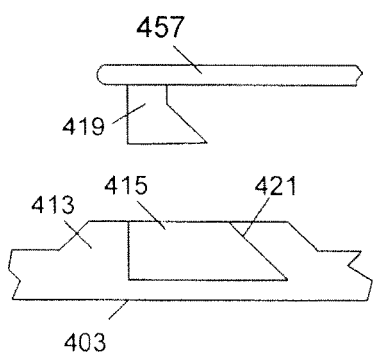
Figure 5:
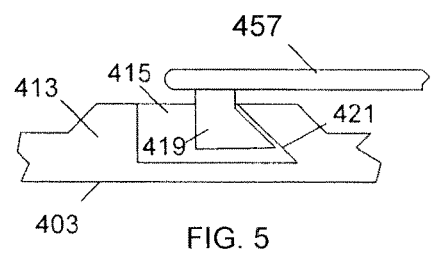

With reference to FIGS. 4 and 5, side views of an embodiment of the adjustment member 457 and an adjustable fastener hole 415 are illustrated. To secure the brace 100 around the forearm, a hook 419 at the end of the adjustable member 457 can be manually pulled to the desired tension and placed over the corresponding hole 415 as shown in FIG. 4. The hook 419 is then placed into the hole 415 as shown in FIG. 5. The tension on the adjustable member 415 will cause the hook 419 to engage the corresponding angled surface 421 within the hole 415 and hold the adjustable member 457 to the hole 415. The patient can also release the hook 419 from the hole 415 by pulling the end of the adjustable member 457 out of the hole 415 to release the adjustable member 457. The user can then remove the brace or reposition the adjustable member 457.

In an embodiment, as illustrated in FIG. 1, the plurality of fastener holes 415 can be configured in different distances from the second edge 411. Positioning the adjustable member 457 in different holes 415 can allow the user to control the circumference of the brace 100. Thus, the adjustable member 457 can be moved horizontally over the holes 415 until the hook 419 is placed over the proper hole 415 that provides the desired tension. The hook 419 can then be placed in the hole 415 so that the adjustable member 457 will be secured in place. In this case, the holes 415 towards the finger end of the brace 100 are closer to the second edge 411 and will produce a looser fit and the holes 415 towards the wrist section of the brace 100 are farther from the second edge 411 and will produce a tighter fit. In other embodiments, the holes 415 can be arranged in any other configuration that provides multiple adjustable member 457 settings. The brace 100 can be adjusted by the patient as the hand expands and contracts due to changes in temperature, atrophy, swelling due to injury, comfort or any other reasons.

Figure 6:
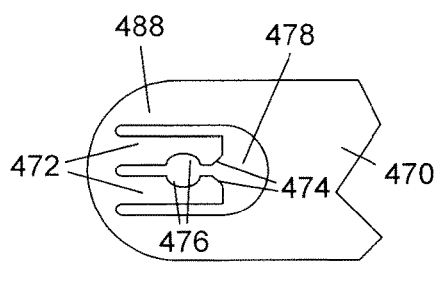
Figure 7:
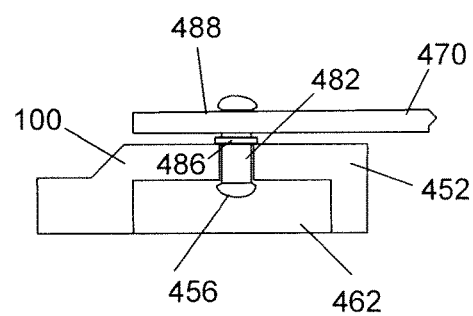

FIGS. 6-7 illustrate another connection mechanism for coupling the adjustable member 470 to the brace 100. In this embodiment, the end of the adjustable member 470 can have a clip mechanism 488 at one end and a hook 419 at the opposite end as illustrated in FIGS. 4 and 5. The clip mechanism 488 can include two elongated prongs 472 that have tapered ends 474 and clip holding sections 476. The ends of the prongs 472 can be coupled to the adjustable member 470 and may be flexible to allow for some elastic deflection. The clip mechanism 488 can also have an open space 478 adjacent to the tapered ends 474. The clip mechanism 488 can be clamped around a pin 482 having flared tips 458 at the ends and a center flange 490. The pin 482 can be inserted into a hole in the brace 100 having an inner diameter that is smaller than the outer diameter of the flared tip 458 and the lower flared tip 458 can extend into a recessed portion 462. The flange 486 can rest against the outer surface of the brace 100 to keep the upper portion of the pin 482 extending away from the brace 100. The upper portion of the pin 482 can be placed into the open space 478 and clip mechanism 488 can be moved around the pin 482 so the prongs 472 spread apart and slide under the upper flared tip 458 until the upper portion of the pin 482 is positioned within the clip holding sections 476 of the prongs 472. The clip holding sections 476 of the prongs 472 will hold the clip mechanism 488 in place on the pin 482.

Figures 8, 9:
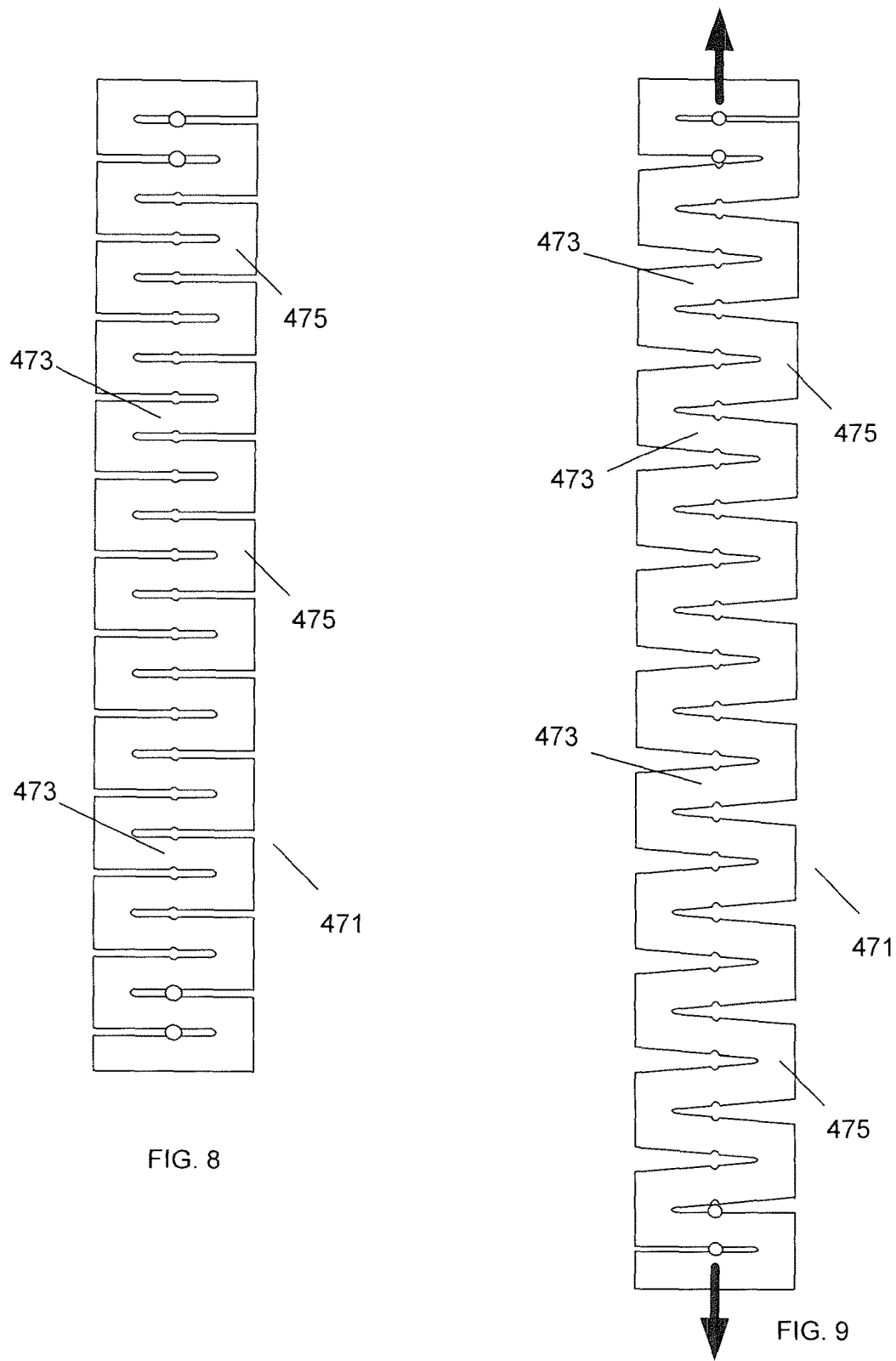
FIGS. 8-9 illustrate an embodiment of an elastic member.

Because the adjustable member 457 can be a linear structure that is made of a relatively inelastic material, the adjustable member 457 may not stretch. Thus, the tension will change if the portion of the limb surrounded by the adjustable member 457 changes due to swelling or shrinking. In other embodiments, it may be desirable to secure the brace 100 to the limb with an elastic adjustable member that can vary in length. For example with reference to FIG. 8, an embodiment of an elastic member 471 in a normal compressed state is illustrated. In this embodiment, the elastic member 471 has a serpentine shape that has a plurality of members 473 that are substantially perpendicular to the length of the elastic member 471. The ends of the members 473 can link the adjacent connectors 475 and run parallel to the length of the elastic member 471. With reference to FIG. 9, when tension is applied to the elastic member 471, the connectors 475 can elastically bend which allows the elastic member 471 to stretch in length. When stretched, the members 473 can be angled so that they are no longer parallel to each other. When the tension is released, the elastic member 471 will return to its original shape as shown in FIG. 6. Securing the brace to limb with the elastic member 471 can provide a more comfortable fit for the patient.

Figure 10:
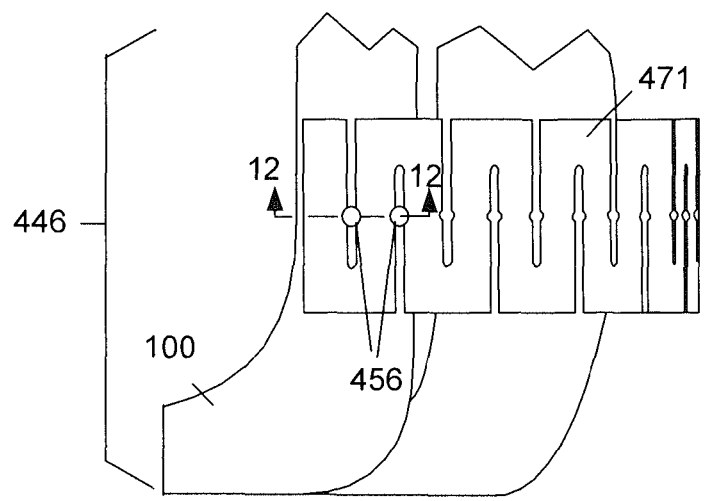
FIGS. 10-12 illustrate an elastic member coupled to the brace.
Figure 11:
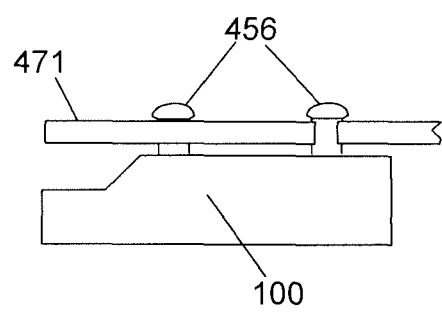
Figure 12:
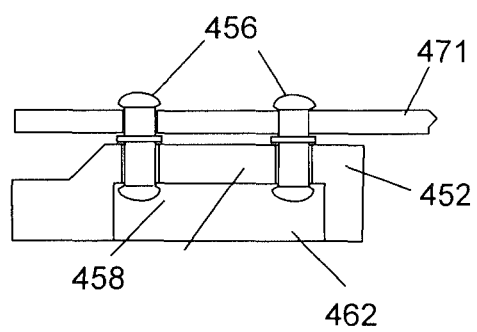

With reference to FIGS. 10-12, the elastic member 471 can be used on the brace 100 in place of the adjustable member 457 illustrated in FIGS. 1-3. FIG. 10 illustrates a view of the elastic member 471 on the proximal portion 446 of the brace 100. The adjustable member 457 can be a separate component that is attached to the brace 100 but may not be an integrated part of the brace structure. With reference to FIG. 11, the adjustable member 471 can be a separate structure that is attached to the brace with one or more fastening pins 456 that were described above with reference to FIG. 7. This design allows the position of the elastic member 471 to be change as necessary to provide a comfortable tension and fit for the patient. The elastic member 471 may be available in different lengths or if there is excessive length, the elastic member 471 can be cut to the proper length. In an embodiment, the elastic member 471 can be stocked in various lengths and attached to the brace 100 after it has been fabricated. In an embodiment, the elastic member 471 can be created as an integrated portion of the brace 100. For example, if the brace 100 is fabricated using a 3D printing machine, the elastic member 471 can be formed with the brace 100 as a single integrated structure.

Figure 13:
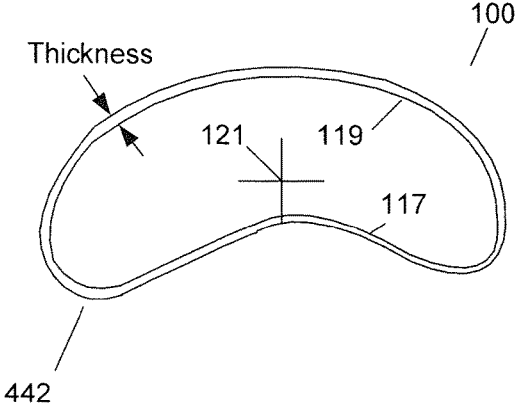
FIGS. 13-14 illustrate axial views of an embodiment of a bikini brace.
Figure 14:
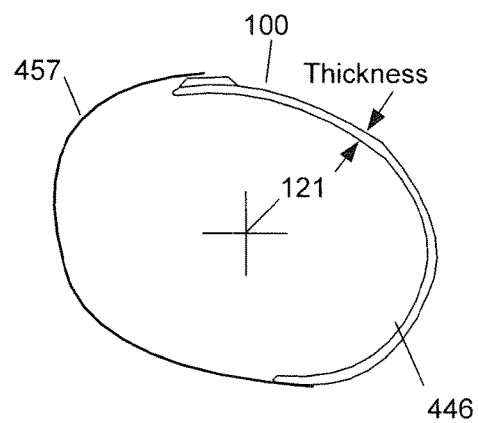

FIG. 13 illustrates a front view of the brace 100 at the distal hand section 442 and FIG. 14 illustrates an end view of the brace at the proximal end 446. The bikini brace 100 has an inner surface that corresponds to a digital representation of the arm and defines a center axis 121. The bikini brace 100 can allow the hand to rotate about the center axis 121. Because the upper section 119 and the lower section 117 fit closely around the hand, the distal portion 115 can remain stationary on the hand, but the middle portion 113 and the proximal portion 111 can rotate around the forearm of the patient if the wrist is rotated about the center axis.

With reference to FIGS. 1 and 2, there are various features that make the inventive bikini brace comfortable to wear. The inner surface 103 of the brace 100 can correspond to a digital representation of the injured limb and closely match the surface measurements of the patient limb so that the brace 100 will provide a custom and personal fit for the patient's limb. Because the brace 100 is thin it can be easily worn under clothing. A bikini arm brace 100 can have thickness that is between about 0.05 inch and 0.50 inch. The brace can have a width between about 0.5 inch and 2 inches. Because the brace 100 is thin and light weight and may look more like an ornamental object than a medical device, the patient is more likely to wear the inventive bikini brace. For clear figures, the fenestrations have not been illustrated in the brace illustrations. However, in embodiments, the fenestrations can be a pattern or small or larger holes that extend through the thickness of the brace 100 and allow air to circulate to the portions of the limb covered by the brace 100.

Figure 15:
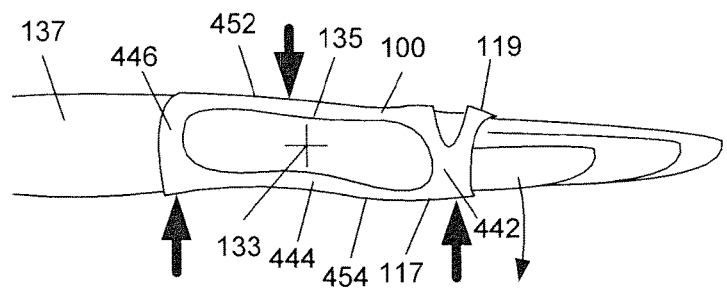
FIGS. 15-16 illustrate side views of an embodiment of a bikini brace on an arm.
Figure 16:
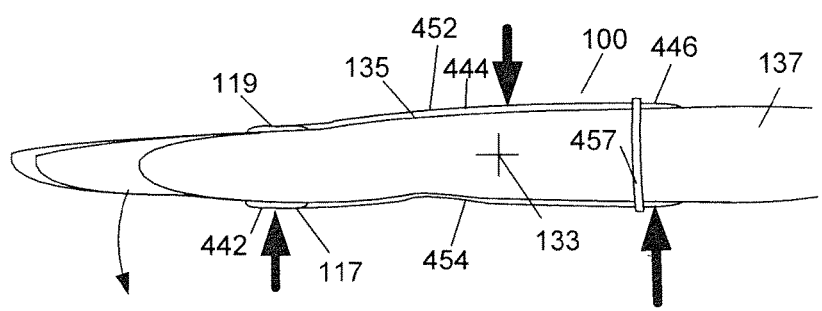

FIGS. 15 and 16 illustrate side views of an arm 137 in an embodiment of the bikini brace 100. FIG. 15 illustrates a side view of the right hand from the small finger side of the hand and FIG. 16 illustrates a side view of the right hand from the thumb side of the hand. As discussed, the distal portion 442 fits around the hand 135, the middle portion 444 is positioned around the wrist 133 and the proximal portion 446 fits around the forearm 137. If the patient attempts to rotate the hand 135 about the wrist 133, the brace 100 will resist this motion. More specifically, the palm of the hand 135 will press against the lower section 117 of the distal portion 113 which will cause the middle section 115 to press down against the wrist 133 these forces will also rotate the brace 100 so that the proximal portion 111 presses up on the lower surface of the forearm 131.

The rigidity of the brace 100 will determine the amount of bending of the limb that is possible. If the brace 100 has a high axial rigidity the arm 137 will not bend about the wrist. However, if the brace 100 can be made of an elastic material, some bending of the arm 137 may be possible. By know the mechanical properties of the material being used and the brace design dimensions, the bending characteristics can be designed into the brace. Thus, the brace 100 can be fabricated so that the axial rigidity is within a specific range based upon the needs of the patient. For example, a brace made for an adult may need to be more rigid than a brace made for a small child in order to provide the required limb movement resistance. The configuration of the elongated portion 452 on the upper and the elongated portion 454 on the lower sides of the brace 100 as opposed to being in the middle or on the same side of the brace 100 can improve the rigidity of the brace 100 against the illustrated wrist movement. The illustrated bending forces can result in the upper elongated portion 452 can be in tension and the lower elongated portion 454 can be in compression. The bending properties of the upper elongated portion 452 and the lower elongated portion 454 can control the bending rigidity of the brace 100.

With reference to FIGS. 10 and 11, a hand and specific anatomical structures are illustrated. FIG. 10 illustrates a palmar side of the hand and FIG. 11 illustrates a dorsal side of the hand 135. The anatomical structures include: the proximal phalanx segments 221 of the fingers, the palmar digital creases 231, the distal palmar crease 223, the proximal palmar crease 225, the thenar crease 227 and the wrist crease 229. Because the fingers bend towards the palmar side of the hand 135, these creases may only be visible on the palmar side of the hand 135. The hand 135 may also include anatomical points that can be marked with stickers or any other type of markings that can improve the accuracy of the measurements for these points. These marked anatomical points can include: finger knuckles 224, the thumb knuckle 226, radial styloid 228, and the ulnar styloid 230. The knuckle and styloid points may be marked on either side of the hand. In an embodiment, the knuckle and styloid points can be marked on one side of the hand 135 and the system can identify these points and points for these anatomical features on the opposite side of the hand. For example, if the knuckle and styloid points are identified on the surface of the dorsal side, the system can process this information and also identify the locations of the knuckle and styloid points on the surface of the opposite palmar side of the hand 135. The system can also function in the reverse manner with the system identifying points marked on the dorsal side of the hand based upon markings on the palmar side of the hand In an embodiment, the system can use the location information to design a portion or the entire the brace. The system can design the brace either with additional input from a brace designer or fully automatically.

By identifying and referencing these visible anatomical features of the hand during the design process, the bikini brace can be designed to cover specific areas of the hand to prevent specific types of movement or avoid certain areas of the hand to allow movement of specific joints or parts of the hand or limb. In an embodiment, the photographic process used to create a digital representation of the body may be able to identify these features and provide graphical identifications of these features on a display coupled to a design computer. The brace can then be designed to restrict or accommodate movement of specific areas of the hand.

Figure 19:
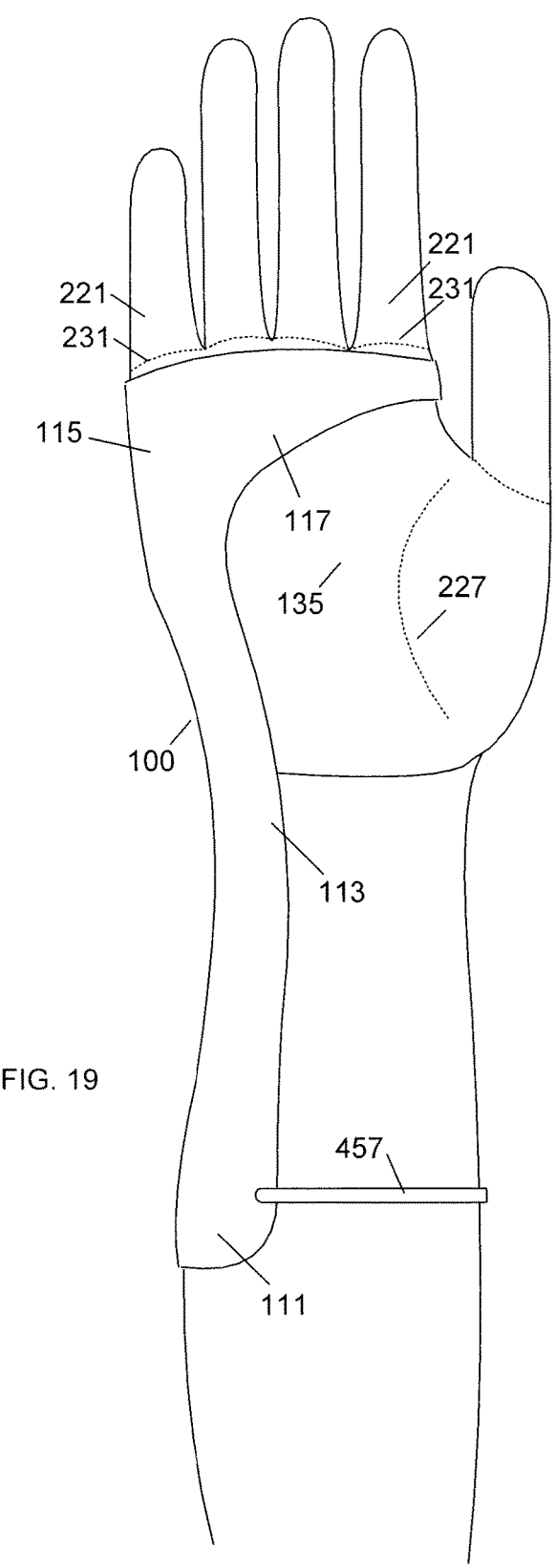
FIG. 19 illustrates a view of a bikini brace on a hand.

With reference to FIG. 19, a palmar view a brace 100 on an arm is illustrated. The brace 100 can prevent the hand 135 from moving in radial deviation. The distal portion 115 can press against the hand 135 which can cause the middle section 113 can press against the wrist 133 and the proximal portion 111 to press against the forearm 137. In contrast, the illustrated brace 100 may not resist movement of the hand 135 in ulnar deviation. The distal portion 115 may not surround the thumb side of the hand 135. Thus, the hand 135 may be free to rotate in ulnar deviation. In other embodiments, the brace may surround the hand 135 and prevent or restrict rotation in ulnar deviation. The inner surface of the distal section 117 can correspond to the palm portion of the hand 135 and may closely match the surface measurements of the hand 135. The distal section 117 may cover the distal palmar crease 223 and the proximal palmar crease 225, but may not cover the proximal phalanx segments 221 or the palmar digital creases 231. Therefore the movement of the fingers may only be partially restricted by the bikini brace 100. Similarly, since the lower section 117 does not extend over the thumb or the thenar crease 227, the movement of the thumb is also not restricted. The brace 100 does cover the wrist crease and the brace 100 resists or prevents the rotation of the hand about the wrist as illustrated in FIGS. 15 and 16.

Figures 20, 21:
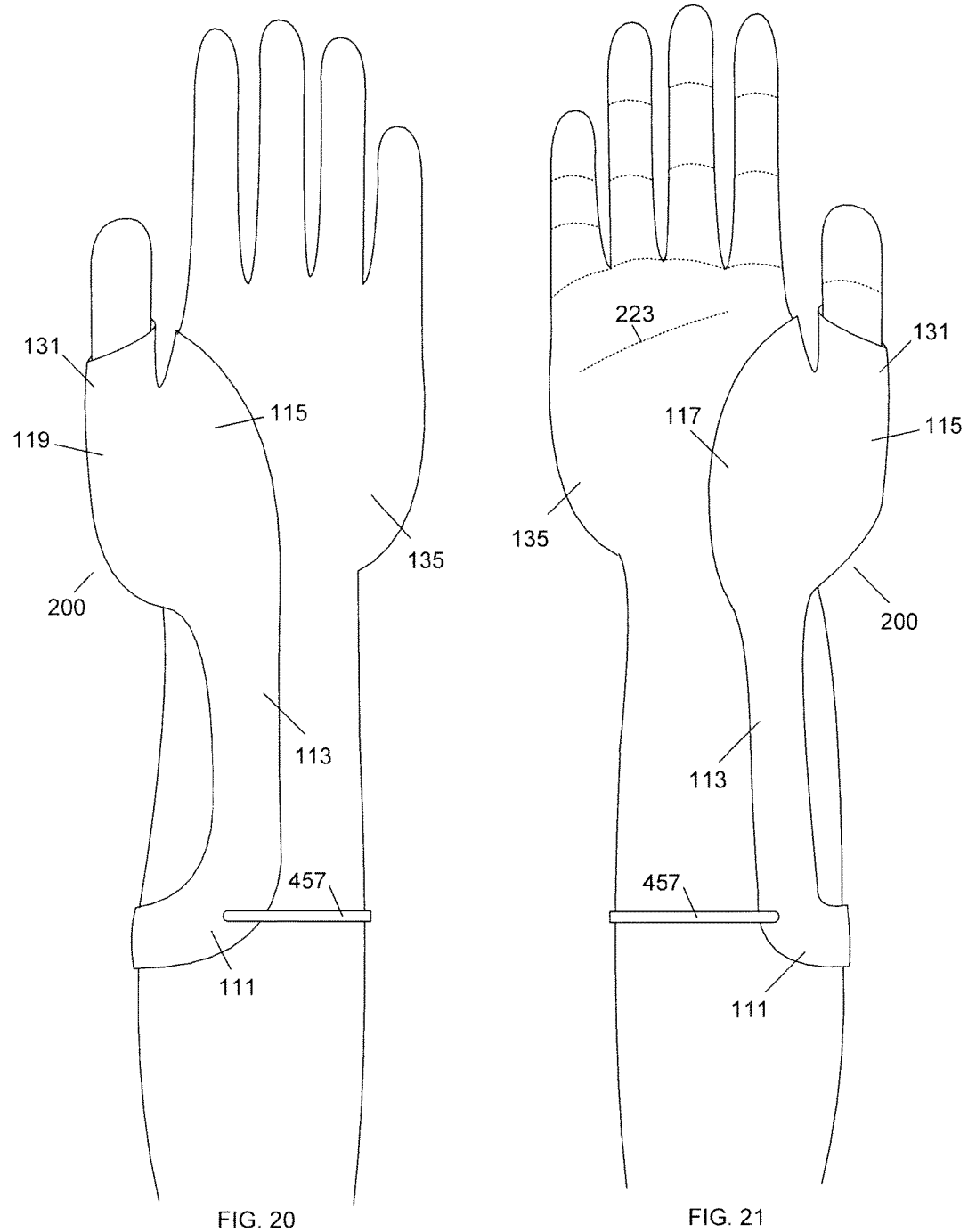
FIGS. 20-21 illustrate views of a bikini brace that restricts thumb movement.

With reference to FIGS. 20 and 21, in an embodiment, the bikini arm brace 200 restricts the movement of the thumb is illustrated. FIG. 20 illustrates a top dorsal view of the bikini brace 200 and FIG. 21 illustrates a bottom palmar view of the brace 200. In this embodiment, a distal portion 115 of the bikini brace 200 includes a thumb section 131 that extends up a portion of the thumb from both the lower section 117 and the upper section 119. Since the thumb is surrounded by the thumb section 131, the bikini brace 200 restricts the movement of the thumb relative to the hand. Because the brace 200 can have an inner surface that corresponds to a digital representation of the hand, the thumb section 131 can have a very close fit with the thumb that is comfortable but also completely restricts the thumb movement. In this embodiment, the distal section 115 may also cover the thenar crease to further restrict movement of the thumb. In order to place the brace 200 onto the arm, the hand may first be placed into the distal portion 115 with the thumb placed through the thumb hole 135. The middle section 113 and the proximal section 111 can then be positioned around the arm and the adjustable member 457 can then be placed around the forearm to secure the brace 200 to the forearm.

Figures 22, 23:
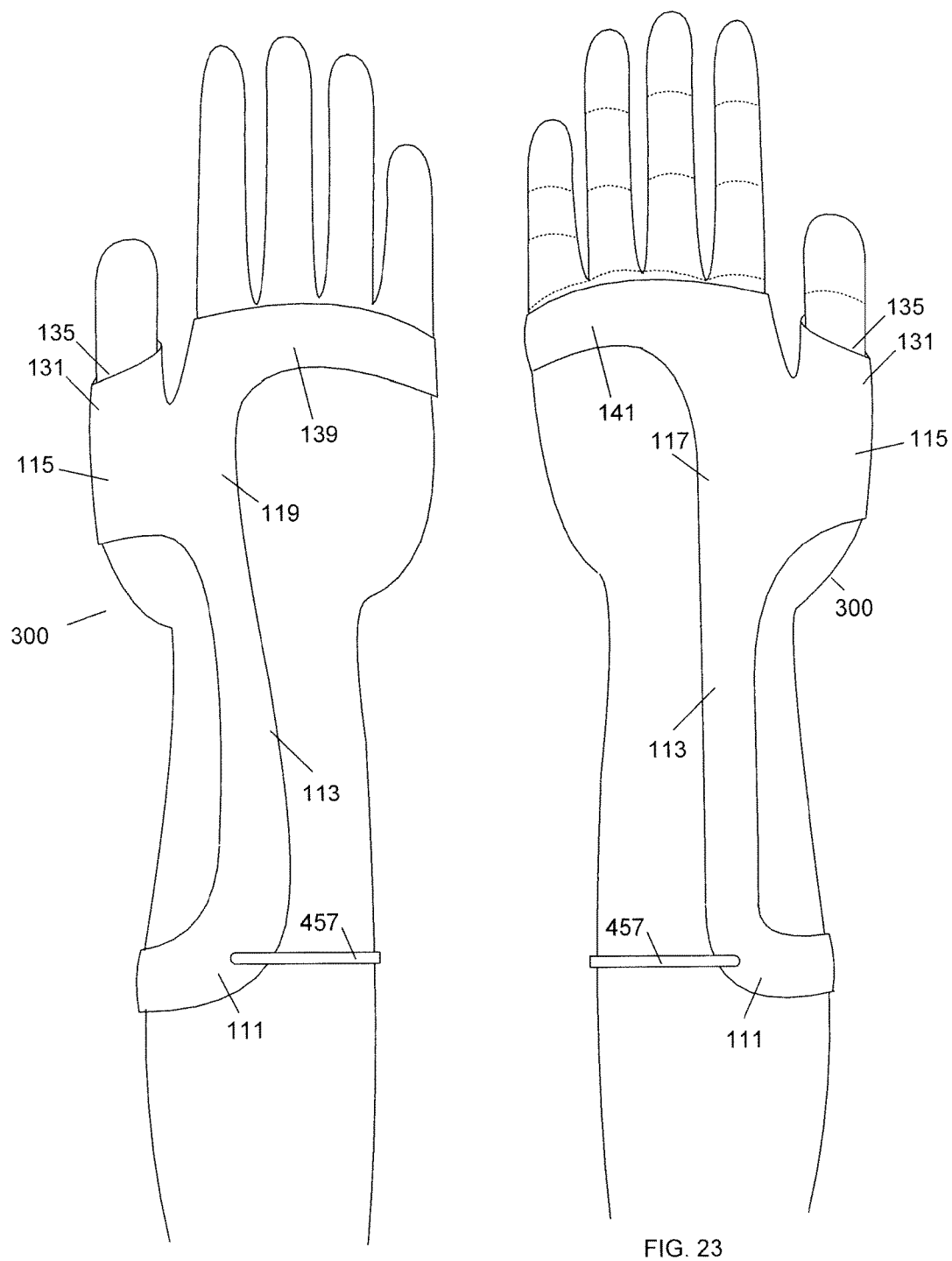
FIGS. 22-23 illustrate views of a bikini brace that restricts thumb and finger movement.

With reference to FIGS. 22 and 23, an embodiment of a bikini arm brace 300 is illustrated that prevents movement of the hand and the lower thumb and restricts the movement of the fingers. In this embodiment, the distal portion 115 may extend around the fingers of the hand and the brace 300 may also include a separate thumb section 131 and a hole 135. The lower surface 117 may also include a lower finger section 141 that is adjacent to the proximal phalanx segments 221 of the fingers. The upper section 119 can include an upper finger section 139 that extends over the knuckles of the hand. The thenar crease may also be covered by the distal portion 115. Thus, the hand movement may be more restricted by the bikini brace 300 than the other illustrated braces 100 and 200. In order to place the brace 300 onto the arm, the hand may first be placed into the distal portion 115 with the thumb placed through the thumb hole 135 and the fingers placed between the lower finger section 141 and the upper finger section 139. The middle section 113 and the proximal section 111 can then be placed around the arm. The adjustable member 457 can then be placed around the forearm and attached as described above to secure the brace 300 to the forearm.

In an embodiment, the bikini braces disclosed by the application are fabricated using a 3D printing machine, as a single integrated structure. Although, the braces are shown for hands and forearms, in other embodiments, the inventive braces may also be designed and used for any other portion of the patient's body including elbows, feet, legs, ankles, knees, back, neck, shoulders, and other portions of the body.

The brace can have a smooth inner surface that corresponds closely to the patient's body and may also have an integrated construction. The cast or brace can be designed by an industrial designer using a Computer Aided Design (CAD) computer program. The mechanical data for a patient can be obtained from visible or infrared (IR) light photographs of the patient's body or limb. This body topography can be determined from the photographs and the topography data is then digitized and input into a CAD program that is referenced to design the cast or brace. An example of a suitable CAD program is Pro/Engineer by Parametric Technology Corporation. Other CAD software includes: SolidWorks by SolidWorks Corporation a subsidiary of Dassault Systèmes, S. A. For simplicity, the inventive custom brace, cast or device will be described as a leg brace, however the same processes can be used to form an arm or back brace or any other body brace, cast or device. The brace can be a hard and strong structure that is designed to surround and support the injured portion of the body or limb.

For example, a leg brace is created for a patient using a CAD system. The leg brace can include an upper leg, knee, lower leg, and foot and have an interior surface that matches the mechanical dimensions and surface contours of the patient's leg. In order to accurately create an interior surface that matches the patient's leg, the surface counters of the user's leg are measured. The measurement of the outer surface of the leg can be obtained in several different ways. In a preferred embodiment, a photogrammetry, depth mapping or image correlation technique or other type of photographic surface detection method is used to obtain the outer surface measurements which can be a set of 3-dimensional coordinates that define the outer surface of the patient's leg or any other body part.

Photogrammetry in its broadest sense reverses the photographic process by converting flat 2-dimensional images of objects back into the real 3-dimensional object surface. Two or more different photographs can be required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In other embodiments, a light from a light source that is a known distance from a camera is projected onto a patient and a photograph of the patient is taken. By triangulating each of the points of light, the distances from the camera to each point of light can be determined. In order to triangulate a set of points one must also know the camera positions and aiming angles also called the "orientation" for all the pictures in the set. A process called resection is used to determine the camera positions and aiming angle calculations for each camera. The cameras should also be calibrated so their errors can be defined and removed.

Triangulation is the principle used by photogrammetry to produce 3-dimensional point measurements. By mathematically intersecting converging lines in space, the precise locations of the points can be determined. Photogrammetry can simultaneously measure multiple points with virtually no limit on the number of simultaneously triangulated points. By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point. When a pattern of IR or visible light points are projected onto the patient, triangulation can also be used to determine the locations of these points based upon the distance between the light source and the camera and the detected angles of the points.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have at twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger number of reference points.

In an embodiment, the patient's natural features including: freckles, spots, wrinkles, pores and other features can be used as the reference points. Alternatively, IR or visible light can be projected onto the patient to provide the reference points for photographic measurement. It is also possible to mark the patient's skin with ink markers and in an embodiment, the patient or patient's limb can be covered with a form fitting material such as an elastic cotton tube, stockinette, leotard, body suit.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object, a known distance between cameras or a known distance between a light source and a camera. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars. The patient topography dimensions can also be determined by knowing a distance between two cameras and the angles of lines between the cameras and the points on the patient. From this information, the distances between the cameras and the points on the patient can be determined by triangulation. Similarly, the patient topography dimensions can also be determined by knowing a distance between a light beam source and a camera, an angle of the light beams from a source and the angles of the light points detected by the camera. From this information, the distances between the camera and the light points on the patient can be determined by triangulation. The light can be infrared and the camera can be an infrared camera that produces infrared photographs.

In an embodiment, the inventive method is used to make a cast or a brace for an injured limb. A series of photos are taken of the injured limb. If the bone is broken, fracture should be reduced before the photos are taken. The photogrammetric processing methods described above are then used to obtain the surface coordinates of the injured limb. In order to define common surface points on the limb, reference points can be placed on the limb. The reference points can simply be any contrasting color points, patterns, shapes, objects, symbols or other optical indicators which are easily visible. The reference points can be black or colored ink marks that are placed on the body with a pen. In other embodiments, the reference points can be lights such as visible light, infrared light, points or grids, stickers or objects or any other visible point of reference. For example, circular adhesive stickers which have a contrasting color can be placed on the patient and photographed. The stickers can provide accurate reference points which can be used to produce the digital representation of the patient's limb and/or body. In the preferred embodiment, the reference points are placed and evenly distributed around the entire limb or portion of the body that the brace is being constructed for.

Figure 24:
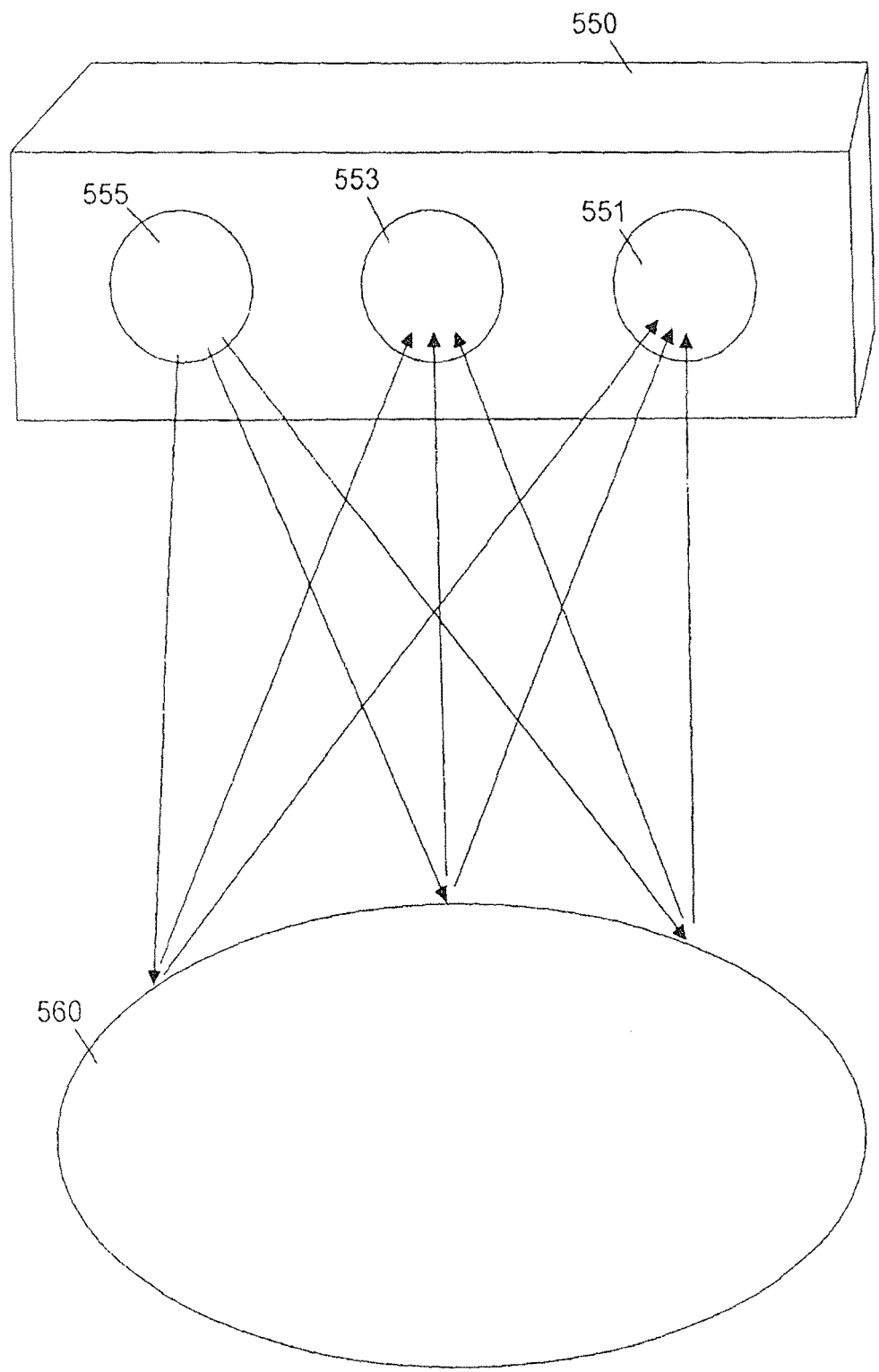
FIGS. 24-27 illustrate IR and visible light photographic systems for detecting a surface of a patient.

With reference to FIG. 24, in an embodiment the three dimensional surface data of a patient can be obtained using an optical device comprising a color image camera 551, an infrared (IR) camera 553 and an infrared (IR) light source 555 coupled to a signal processor. The IR light source 555, IR camera 553 and color image camera 551 can all be mounted on one side of the optical device 550 so that the color camera 551 and IR camera 553 have substantially the same field of view and the IR light source 551 projects light within this same field of view. The IR light source 555, IR camera 553 and color image camera 551 can be mounted at fixed and known distances from each other on the optical device 550. The color image camera 551 can provide color information for the patient's limb 560 or portion of the patient within the viewing region of the camera 551. The IR camera 553 and IR light source 555 can provide distance information for each area of the patient's limb 560 exposed to the IR light source 555 that is within the viewing region of the IR camera 553. The infrared light source 555 can include an infrared laser diode and a diffuser. The laser diode can direct an infrared light beam at the diffuser causing a pseudo random speckle or structured light pattern to be projected onto the patient's limb 560. The diffuser can be a diffraction grating which can be a computer-generated hologram (CGH) with a specific periodic structure. The IR camera 553 sensor can be a CMOS detector with a band-pass filter centered at the IR laser wavelength. In an embodiment, the color image camera 551 can also detect the IR light projected onto the patient's limb 560.

Figure 25:
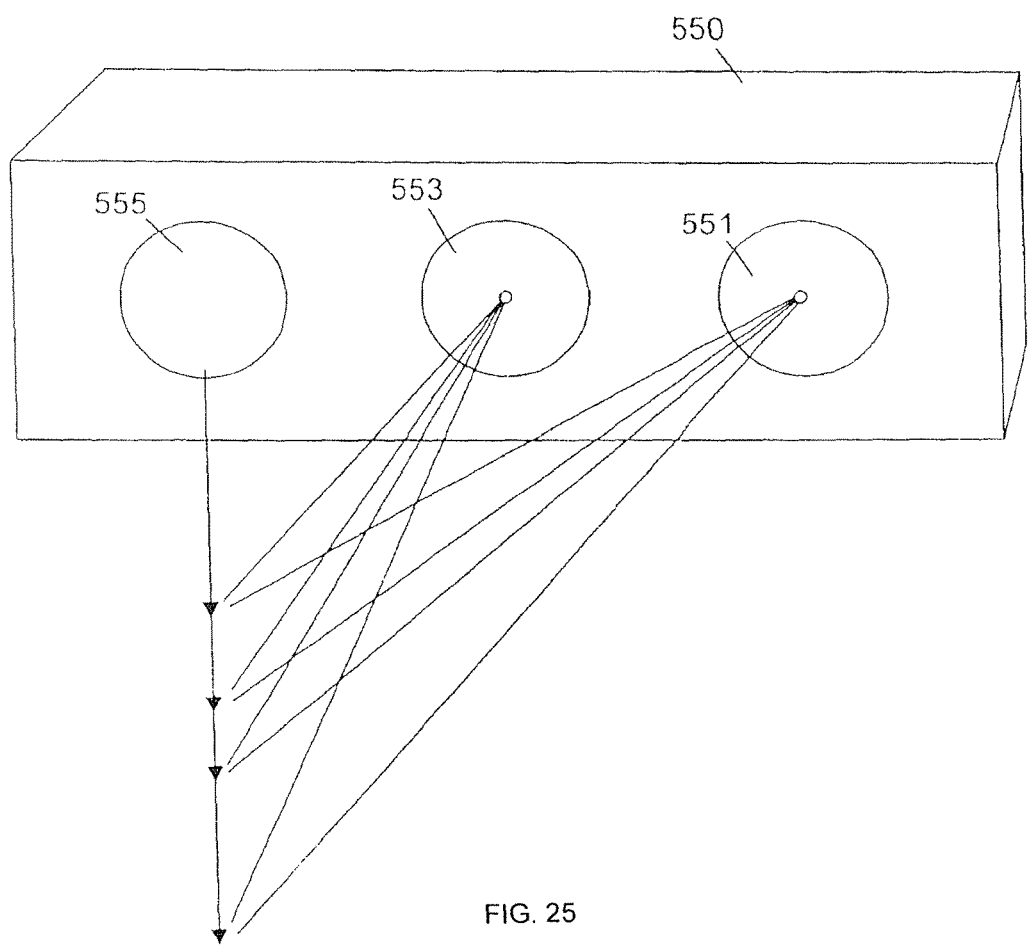

With reference to FIG. 25, the optical device 550 can detect the distance between the infrared camera 553 and the IR light on the patient because the camera 553 sees the patient's limb at a different angle than the infrared light source 555 and the distance between infrared light source 555 and IR camera 553 is defined. The principle of structured light distance sensing is that given a specific angle between IR light source 555 and IR sensor 553 for each point of light on the patient's limb and a distance between the object and the IR light source 555 or IR camera 553 or color camera 551 can be determined by triangulation. The angles of the light points on the patient's limb detected by the IR camera 553 and the color camera 551 will change depending upon the distance of the patient from the optical device 550. In an embodiment, a calibration process can be used to determine the angles of each light point on a plane at different distances from the optical device 550. By knowing the angles and corresponding distances for each point of IR light and distance of the points of light from the optical device 550 can be determined. These distance calculations for an object can also be known as three dimensional mapping. The distance value for each light point can also be matched with the visible color image data so that color and distance information for each pixel of a patient image can be determined and stored.

Because a single picture can capture the patient in a fixed position, the IR light source 555 can be project the IR light on the patient and the IR camera 553 can take a single photograph of the patient 560. The color camera 551 may also simultaneously take a single photograph of the patient's limb 560. In other embodiments, multiple IR or color photographic images can be taken of the patient's limb 560 in different positions and the corresponding image shifts are directly relates to distance from the camera. Each successive photographic image is served as a reference photograph for the next frame calculation so that the movement of the patient can be detected and the changes in the three dimensional mapping can be recorded.

Figure 26:
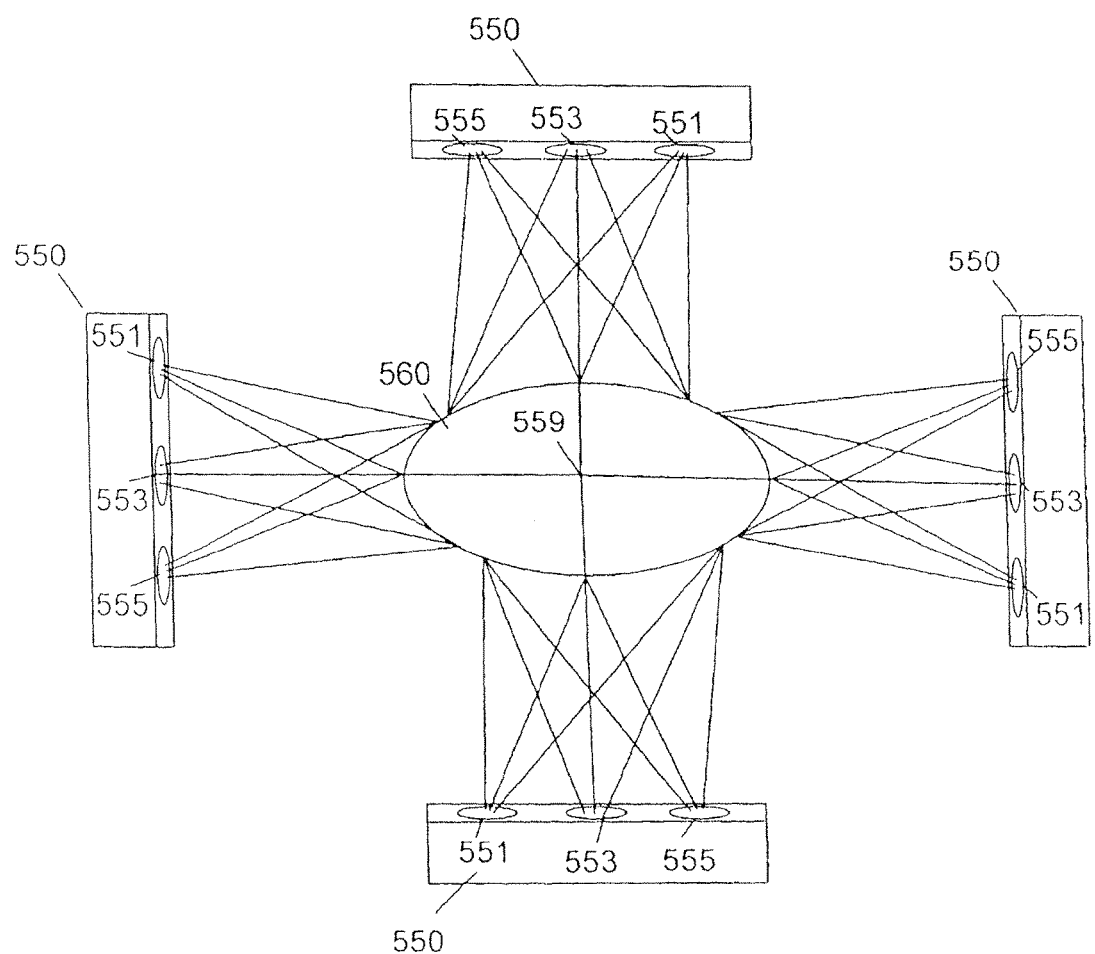

As discussed, the IR camera can detect the light pattern projected onto the patient's limb and through triangulation, the distance between the IR camera and color camera and each point of the light pattern on the patient can be determined. However, the distance information for the points can only determine a three dimensional surface of the patient's limb or a portion of the patient's limb that are detected by the IR camera 553 or the color camera 551. With reference to FIG. 26, in order to determine a three dimensional surface around a patient's limb, multiple optical devices 550 can be placed around the patient and the three dimensional surface information from each of these cameras can be combined to determine the three dimensional surfaces around a circumference of a patient's limb. In an embodiment the IR light from each of the IR light sources 555 can be emitted simultaneously and the photographs from all of the IR cameras 553 and color cameras 551 can be taken simultaneously. In other embodiments, the IR light sources 555 can interfere with the IR cameras 553 that are not part of the same optical system 550. Rather than protecting IR light from all of the IR light sources 555 at the same time, the optical systems 550 can be configured to sequentially illuminate with IR light and photograph the patient's limb 560. A first optical system 550 will emit the IR light and take IR and color photos of the patient's limb 560. The first optical system 550 can then stop projecting IR light onto the patient's limb 560 and the second optical system 550 can then emit the IR light, take IR and color photos of the patient's limb 560. The second optical system 550 can then stop projecting IR light onto the patient's limb 560. This described process can be sequentially repeated for the remaining optical systems 550.

After taking the IR photographs, surface data for different sides of the patient's limb 560 can be combined from the optical systems 550 in various different ways. For example, the multiple IR cameras 553 can produce distance information for the photographed patient's limb 560 that can be combined using a photogrammetry process to determine a full or partial circumferential three dimensional representation of the patient's limb 560. The surface data from the optical systems 550 will include some of the same surface areas of the patient's limb 560 that were also captured by at least two of the adjacent optical system 550. Because the three dimensional shape data is the same, the system can identify these matching surface shapes and combine the surface data to obtain continuous surface data for the photographed portion of the patient's limb 560. In an embodiment, the optical systems 550 can be aligned around the patient 560 with the IR cameras 553 radially aligned in a planar manner and directed towards a center point 559 within a cross section of the patient's limb 560. The optical systems 550 can each produce surface data for a portion of the patient's limb 560. Because the IR photos are taken on a common plane, the surface data from the different optical systems 550 can be joined by determining the distance of the surface data from the center point 559. In an embodiment, a first set of calibration IR and/or color photographs can be taken by the optical systems 550 of a physical center point marker 559 without the patient's limb 560. IR and/or color photos can then be taken of the patient 560. From this information, the position of the center point 559 relative to the surface data of the patient 560 can be determined. By knowing the distances and alignment of the surface data to a common center point 559, the surface data from the different optical systems 550 can be combined. In an embodiment, the optical systems 550 can be arranged on direct opposite sides of the patient's limb 560. Although four optical systems 550 are shown, in other embodiments, two or more optical systems 550 can be used to obtain the surface data for the patient's limb 560. Three optical systems 550 may be required to have some overlapping surface data for the patient's limb 560.

Figure 27:
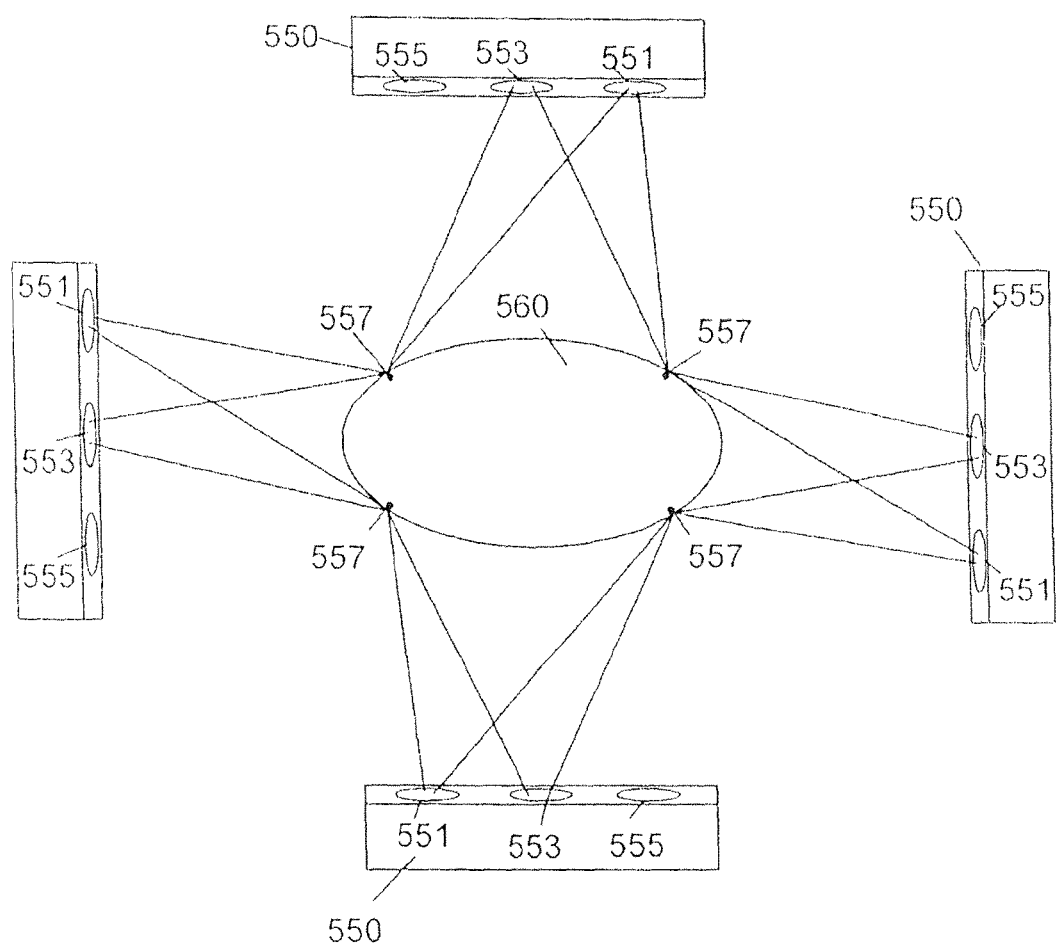

With reference to FIG. 27, in other embodiments the surface data from the optical systems 550 can be combined by using alignment markings 557 on the patient's limb 560. The patient's limb 560 may be covered with a material and a visible or IR marking 557 can be projected onto the patient's limb 560 at locations that are within the field of view of two or more optical systems 550. The color camera 551 may detect both visible and IR markings and the IR camera 553 may only detect IR markings. The optical systems can be able to distinguish the IR light from the IR markings because the shape of the IR marking 557 can be larger or may have a different shape. The surface data from adjacent optical systems 550 can be combined by using a photogrammetry or image correlation process that matches the positions of the markings 557 that are photographed by both optical systems 550.

Figure 28:
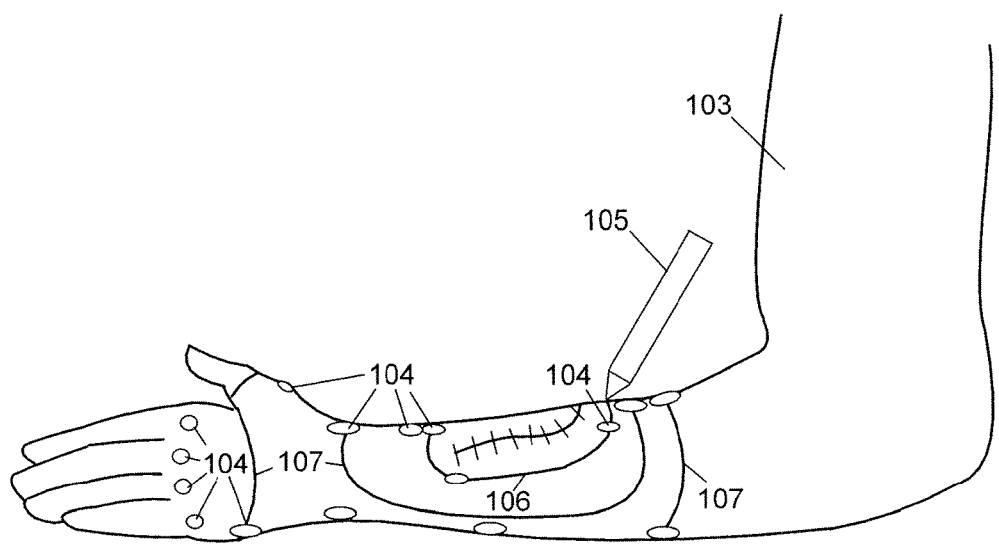
FIG. 28 illustrates a marked patient for detection by the photographic detection system.

In addition to the reference points, the patient can also be marked to define an edge of the brace, a seam of a modular brace or other features. With reference to FIG. 28, the doctor can mark the patient's arm 103 with a pen 105 or with stickers to define the locations of the edge of the brace or other important features. The edge or seam marking can be one or more continuous ink lines 107 that extend around the patient's arm 103. In other embodiments, the edge or seam can be defined by a series of ink marks that define the edge of the brace and are connected during the brace design. Additional ink lines 109 can also be marked on the patient to create edges for the brace pieces. In other embodiments, other marking devices such as stickers can be placed on the patient rather than ink to indicate areas of interest or brace design on the patient.

For example, the patient may have injured areas from an operation that has been closed with stitches and should not be in contact with the rigid brace. By providing an opening in the brace, the patient's stitches will not be pressed against the brace structure. In FIG. 28, the doctor has drawn a circle around or place stickers around or on this portion of the patient's body so that the brace can be designed around this area. The doctor can also make notes on the patient's arm 103. For example, the doctor can write information indicating the location of the injury as well as information indicating the locations of bones, joints, tendons and ligaments. These anatomical locations are important in the design of the brace and are therefore marked on the patient's arm 103. Because photogrammetry uses photographs, the digital pictures will record all of the stickers, ink lines, other ink markings.

In addition to being the proper dimensions, the brace must also be strong enough for the required use. An ankle brace or walking brace may be required to support the user's weight and impact while running or jumping and an arm brace must be able to withstand the normal use forces. In an embodiment, the strength of the brace is determined by the geometry of the brace and the materials used to fabricate the brace. Suitable materials include high strength plastics such as high strength polyamides metals, alloys and composites such as carbon fiber in an epoxy binder.

Figure 29:
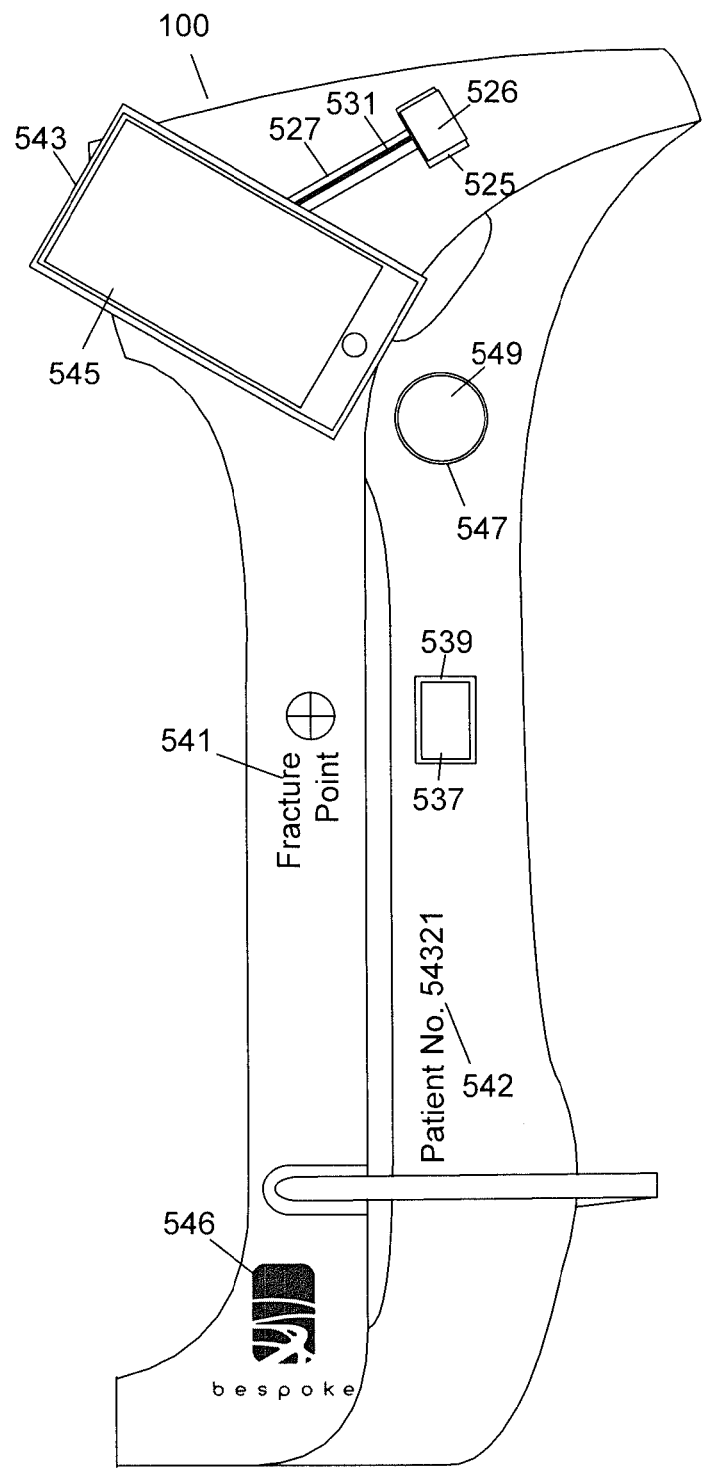
FIG. 29 illustrates markings and/or patient information added to a brace.

In addition to designing the brace to provide support for the patient's limb, additional features can be added to the brace design before fabrications. With reference to FIG. 29, the use of additive fabrication allows unique markings and/or patient information to be added to the brace design and printed directly into the brace during the fabrication process. These markings can include: ornamental images and patterns, patient medical or identification information 542, marks indicating the locations of breaks or fractures 541, the logo for the clinic or manufacturer that provided the brace 546, the date of manufacture, etc.

Other additional features that can be added to the brace design include custom mounts on the brace at locations that are specified by the brace designer or physician. The custom mounts may represent positive protrusions, or negative depressions of combinations thereof. The mounts may support functional or cosmetic devices. An example of a brace mount 543 would be a mount for a device 545 such as: an iPod, iPad, iPhone, cell phone, remote control device or other portable electronic devices. These devices 545 can be difficult to operate with one hand. By securing any of the devices 545 to the brace 100, the patient can operate the device 545 with a free hand, finger or limb. In some embodiments, the positions of these electronic devices 545 can be fixed. In other embodiments, the mounts 543 may be adjustable so that the devices 545 can be optimally positioned by the user.

The mounts on the brace 100 may also be used for other devices including: sensors, stimulators, actuators and/or electronic devices. An example of a stimulator can be a radio frequency bone stimulator 537 for a fracture delayed union. The mount 539 for the stimulator 537 can be added to the brace design over the fracture site. After the brace 100 is fabricated, the stimulator 537 can be easily placed in the mount 539 such that the stimulator 537 can be reproducibly positioned in the required alignment with the bone injury whenever the brace 100 is worn by the patient. In an embodiment the bone stimulator 537 may only be placed in the mount 539 for radio frequency therapy or alternatively, if the stimulator 537 is small, it can be left in the mount 539 more permanently. In other embodiments, the brace 100 may include similar mounts that can be used for electrical stimulator devices that stimulate muscles electrically to reduce disuse atrophy that occurs with prolonged immobilization of a limb.

In other embodiments, the brace 100 can be designed with mounts 547 for sensors 549 that can monitor the physical condition of the patient and/or brace 100. For example, the sensors 549 may include a strain sensor that is coupled to a monitoring device that produces a warning when excess force is applied to the brace 100. The integrated strain sensor can inform the patient of the excess applied force so that to avoid damage to the brace or limb. As the patient heals, the excess force level alarm can be adjusted by the monitoring device. In an embodiment, the monitoring device can be a personal electronic device such as an iPhone 545 that communicates with the sensor 549 wirelessly through low power RF signals. This feature can be beneficial because it can allow the patient to know the force capabilities of the brace 100 and know when excessive force is being applied. The system may adjust the excess force level as the limb heals so that as the patient's limb heals, more force can be applied to the brace 100. This feature may allow for less rigid brace construction since the brace does not have to be designed for a specific maximum working loading and create a more dynamic bracing concept. Other examples of sensor systems in mounts on the brace may include: an ultrasonic system in which a transducer placed in a mount distal to a fracture point on the limb and a sensor placed in a mount proximal to the fracture point. The transduction characteristics can be monitored through the bone to sense the degree of fracture healing.

The described devices that are placed in the mounts can be electrical devices which require electrical power and/or a communications pathway. The brace 100 may also be designed with an integrated system for securing any necessary cables 531 to the brace 100. The cable system can include a recessed area 527 that allows the cable 531 to be held on the brace. The system may also include a mount 525 for a signal connector 526 to secure the connector 526 to the brace 100. This system can prevent the brace 100 from having loose cables or wires that can get caught or interfere with the movement of the brace 100. Because the medical device mounts can be precisely positioned on the brace 100 during the design process, the mounts are integrally formed with the brace 100 during the fabrication process.

All of the described markings and mounts can be added to the design of the brace 100 and incorporated into the brace during the fabrication process without additional processing. No additional work or modification is needed to add the mounts on the brace 100. Thus, even with these added mountings and markings, the production time and fabrication cost for the brace is not increased. The markings and printing can be formed in a surface of the brace in relief on interior or exterior surfaces of the brace. No previous bracing technology has allowed for the precision or easy application of the stimulator technology within low profile bracing 100 and accurate placement of sensors, devices and position information.

Figure 30:
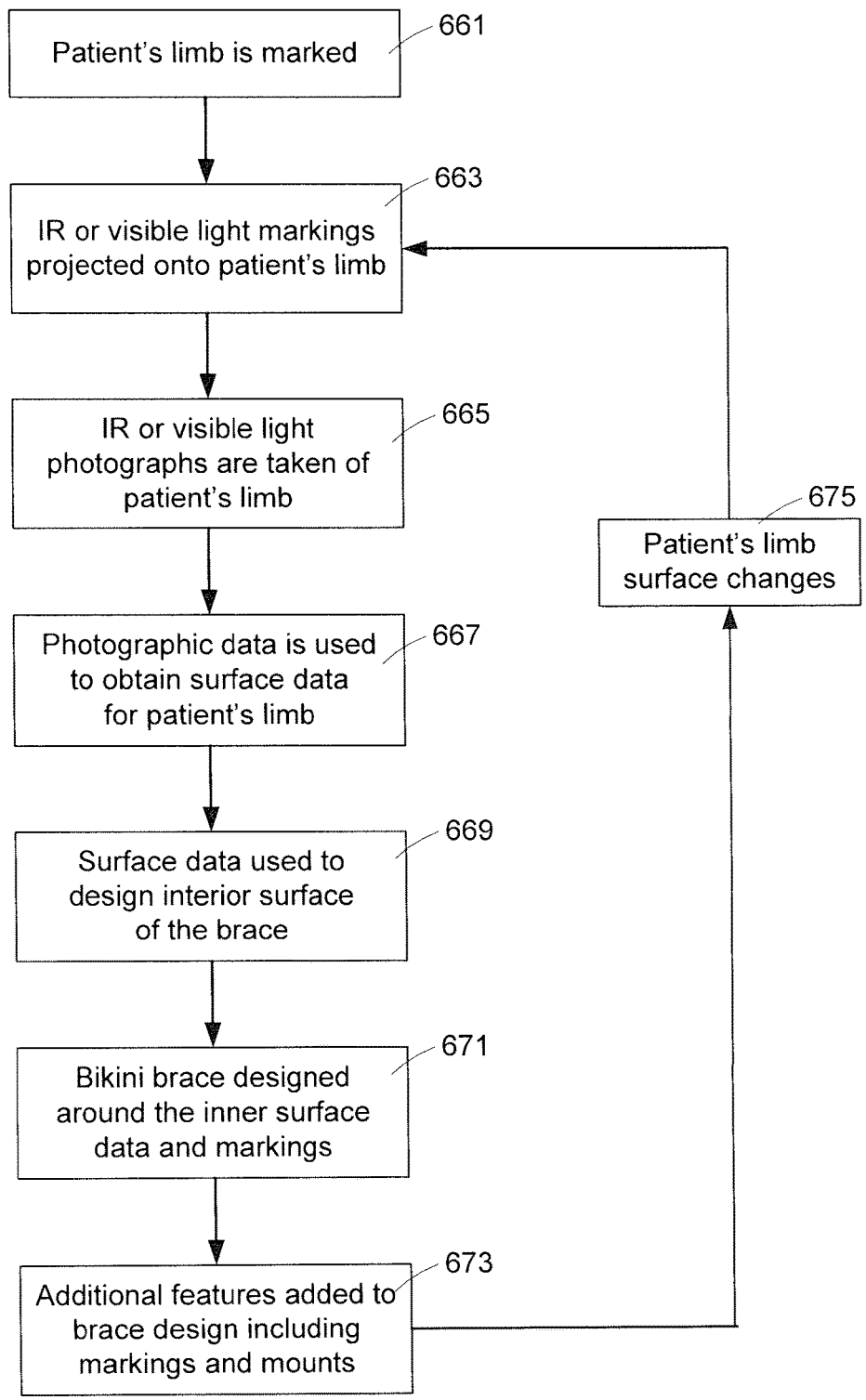
FIG. 30 illustrates a flow chart for fabricating a brace.

With reference to FIG. 30, a flowchart of the process steps for fabricating a brace is illustrated. As discussed above, the patient's limb can be marked 661 with any type of marking device such as a sticker or ink that can be photographed. The markings can indicate a surface location, the location of the injury, edges of the brace, seams of the modular brace, seams of the brace pieces, sensitive areas, locations of stitches, and other body features. The patient's limb can be illuminated with IR or visible light in a pattern such as dots, lines, grids or any other plurality of light points 663. The limb can be photographed with IR and/or visible light cameras as described 665. From the photographic data, the surface data for the patient's limb can be obtained 667. In other embodiments the limb may not be illuminated with an IR or visible light pattern and the surface data can be obtained by the natural markings on the patient's skin.

The surface data can be used to design interior surfaces of a brace 669. With the limb surface data and additional information about the limb injury, the bikini brace can be designed to prevent specific types of movements and avoid contact with specific areas of the limb 671. The brace design can also be modified to include additional marking and mounting features 673. The markings added to the brace design can include information, ornamental designs, injury locations, etc. The mounts added to the brace can include device mounts and instrumentation mounts. If the limb changes in size but remains injured, a new brace may need to be fabricated to provide the required support and restricted movement 675. The described process can be repeated to fabricate a new brace based upon new photographs of the patient's limb.

After the brace or device is designed with the adjustable couplings incorporated, the brace design data is transmitted to a three dimensional fabrication machine that constructs the brace. In an embodiment, the three dimensional fabrication machine is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials by forming planar cross section layers of the structure on a previously formed planar cross section layers. This layered fabrication process is continued from one end of the structure to the opposite end until the structure is completely fabricated.

In order to efficiently produce the described devices, it can be desirable to simultaneously produce as many component parts as possible. Many fabrication machines can produce parts fitting within a specific volume in a predetermined period of time. For example, a brace can fit around the torso of a patient and have a large space in the center. This brace can be made, but it will only make one device. In order to improve the efficiency, the brace can be designed as multiple pieces that are later coupled or fused together. Rather than making a single brace with the large open center area, the described fabrication methods can be used to simultaneously produce components for two or more braces that occupy the same specific volume as a single piece brace. The cost of fabrication using a three dimensional fabrication machine can be proportional to the amount of time required to print the components rather than the raw material costs. The print time can be minimized by placing as many component cross sections into the print area as possible. If a back or limb brace normally has a large open center area the print cost efficiency can be poor. However, if the brace is a modular design, the modular section pieces can be fabricated in a more efficient manner. For example, multiple modular section pieces can be fabricated simultaneously with the convex surfaces of a first section piece adjacent to concave surfaces of another section piece. By laying out the components in an efficient production manner for fabrication by an additive material machine, the cost of fabrication can be significantly reduced. The components can then be assembled and coupled or fused together to form the brace. In an embodiment, the inner surface of the brace can be manufactured with a high resolution so that the inner surface is very smooth.

When the brace is fabricated using a three dimensional printing machine, the brace is formed by depositing a plurality of parallel planar layers of material with each layer fused to the adjacent layer. Each layer of material used to form the brace can have a predetermined and uniform thickness. In order to optimize the efficiency of the brace fabrication, it can be desirable to minimize the number of parallel planar layers used to create the brace. This minimizes the number of layers that are formed to create the brace and optimizes the fabrication efficiency. In an embodiment, the brace design information can be placed in a virtual box having square corners. The parallel planar layers formed to create the brace can be perpendicular to the shortest dimension of the brace which can be the thickness of the box.

Figure 31:
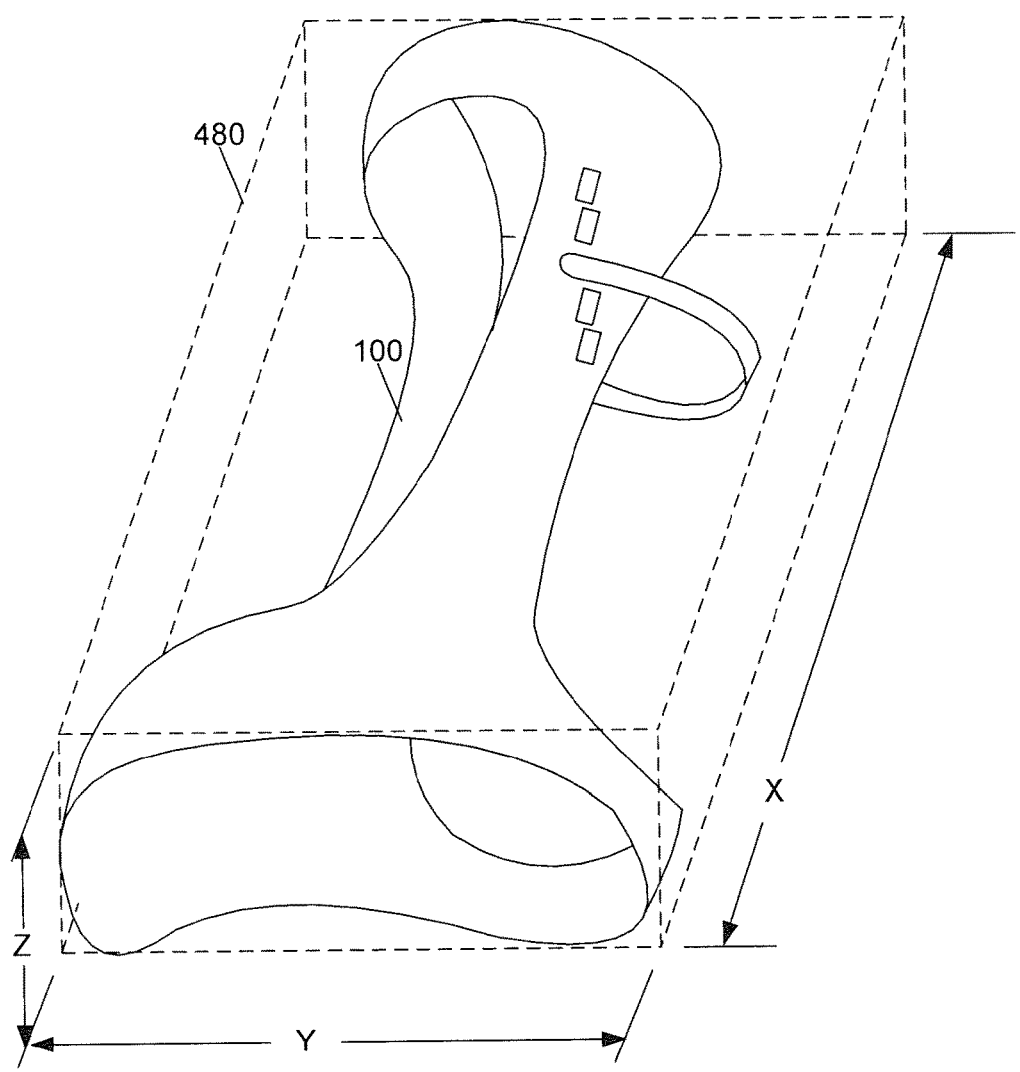
FIGS. 31-32 illustrate embodiments of the bikini brace design data in a virtual box prior to fabrication with a three dimensional printer.

For example, with reference to FIG. 31, a bikini brace 100 is illustrated in a virtual box 480 having square corners and planar sides. The brace 100 can be an elongated structure that extends from the forearm to the hand and define the length axis. The length of the box 480 X can be the longest dimension of the brace 100 and a thickness of the box 480 Z can be the shortest dimension of the brace 100. In an embodiment, the parallel planar layers that are fused to form the brace 100 can be parallel to the length axis, X. In an embodiment, the parallel planar layers that are fused to form the brace 100 are substantially perpendicular to the thickness axis Z which can be the smallest overall dimension of the brace. In another embodiment, the parallel planar layers that are fused to form the brace 100 are substantially parallel to the width axis Y. In other embodiments, multiple braces 100 can be fabricated simultaneously in the same virtual box 480. By utilizing more volume within the same virtual box 480 or a similar sized virtual box, the braces 100 can be fabricated more efficiently since the time for fabrication can be directly proportional to the volume of the virtual box 480.

Figure 32:
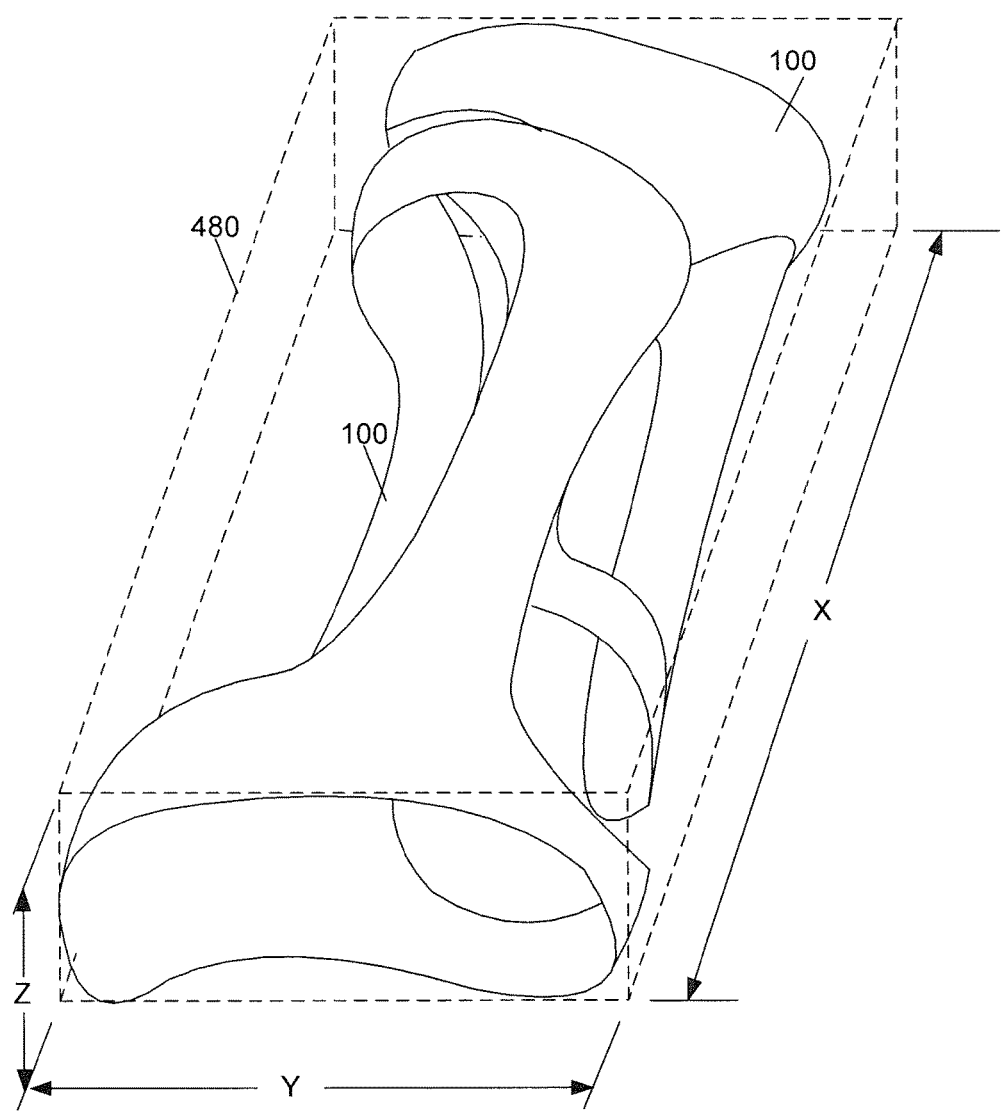

In other embodiments, it is possible to further improve the fabrication efficiency. With reference to FIG. 32, a first bikini brace 100 and a second bikini brace 100 are both illustrated in the virtual box 480. In this embodiment, the first bikini brace 100 can be for a first patient and the second bikini brace 100 can be for a second patient. The first bikini brace 100 and the second bikini brace 100 can be arranged in a nested configuration within the virtual box 480. The efficiency of fabrication can be proportional to the number of bikini braces that can be created within a volume. Thus, if two bikini braces 100 can be created in the same virtual box volume, the efficiency of the fabrication is effectively doubled. In other embodiments, it may be possible to include three or more braces 100 within a virtual box volume that is not significantly larger than the virtual box 480.

After the bikini brace has been formed, additional processing can be performed on the inner surface to increase the smoothness. The inner surface can be tumbled, sanded, polished, or other processes can be used to create the smooth inner surfaces of the brace. These processes can be performed by hand or by a machine. In other embodiments, a filler material can be deposited on the inner surface of the brace shell to create a smooth surface. For example, the inner surface may be painted and the paint may fill the uneven surfaces and dry to a smooth surface. Alternatively, the inner surface can be heated to cause the brace material to reflow and create a smooth inner surface. The inner surface can have a The use of a photographic process has many advantages over other surface scanning technologies such as laser scanning. The process for transposing the locations of features from the patient to the brace or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photographic equipment is also portable, so it can be easily transported to patient's location. The digital data can then be transmitted electronically to a fabrication machine located at a guild. Alternatively, the digital device data can be recorded onto a disk and transmitted to the fabrication machine.

The illustrated braces provide the required support and protection for the patient while minimizing all unnecessary structural components. This minimalistic design matches the patient's anatomy and provides a more comfortable fit. These braces are also lighter in weight than traditional braces and provide greater ventilation. Although, the braces are shown for hands and forearms, in other embodiments, the inventive braces can also be used for any other portion of the patient's body including elbows, feet, legs, ankles, knees, back, neck, shoulders, and other portions of the body.

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the following claims reflect, inventive aspects lie in less than all features of any single foregoing disclosed embodiment.

What is claimed is:

1. A custom brace comprising:
a custom brace body that is adapted to surround a portion of the forearm of the patient, the custom brace body comprising:
a rigid upper elongated beam that extends along a length of a dorsal side of the custom brace;
a rigid lower elongated beam that extends along a length of a palmar side of the custom brace;
a rigid distal hand portion that is adapted to circumferentially surround a plurality of finger knuckles of the patient, the rigid distal hand portion coupled to distal ends of the upper elongated beam and the lower elongated beam;
a rigid proximal forearm portion that is adapted to partially surround the forearm, the rigid proximal forearm portion coupled to proximal ends of the upper elongated beam and the lower elongated beam; and
an inner surface of the brace body that corresponds to a digital representation of the limb of the patient;
wherein the rigid distal hand portion and the rigid proximal forearm portion are only coupled by the rigid upper elongated beam and the rigid lower elongated beam, the rigid upper elongated beam and the rigid lower elongated beam are spaced from each other and the rigid proximal forearm portion does not surround the forearm; and
wherein the rigid upper elongated beam, the rigid lower elongated beam, the rigid distal hand portion, and the rigid proximal forearm portion are formed as a single unitary structure.

2. The custom brace of claim 1 wherein the distal hand portion of the brace body is adapted to partially restrict movement of fingers.

3. The custom brace of claim 1 wherein the distal portion of the brace is adapted to surround a thumb portion of the limb.

4. The custom brace of claim 1 wherein a width of the brace body at the proximal portion is greater than 0.5 inch and less than 2 inches.

5. The custom brace of claim 1 wherein the inner surface of the brace body includes at least one convex surface.

6. The custom brace of claim 1 wherein a thickness of the brace body is greater than 0.05 inch and less than 0.50 inch.

7. The custom brace of claim 1 further comprising:
an adjustable member that is adapted to secure a portion of the brace to the limb.

8. The custom brace of claim 7 wherein the adjustable member is elastic.

9. The custom brace of claim 7 wherein the adjustable member includes a hook for securing a portion of the adjustable member to the brace.

10. The custom brace of claim 1 wherein the brace body is fabricated from a plurality of fused planar layers that are parallel to each other.

11. The custom brace of claim 10 wherein the brace defines a center axis and the plurality of fused planar layers are approximately parallel to the center axis.

12. A custom brace comprising:
a custom brace body is adapted to surround a plurality of finger knuckles of the patient and extend along the forearm of the patient to at least partially immobilize the arm of the patient, the custom brace body comprising:
a rigid upper elongated beam that extends along a length of a dorsal side of the custom brace;
a rigid lower elongated beam that extends along a length of a palmar side of the custom brace;
a rigid distal hand portion that is adapted to circumferentially surround a plurality of finger knuckles of the patient, the rigid distal hand portion coupled to distal ends of the upper elongated beam and the lower elongated beam;
a rigid proximal forearm portion that is adapted to partially surround the forearm, the rigid proximal forearm portion coupled to proximal ends of the upper elongated beam and the lower elongated beam; and an inner surface of the brace body that corresponds to a digital representation of the arm of the patient;

wherein the rigid distal hand portion and the rigid proximal forearm portion are only coupled by the rigid upper elongated beam and the rigid lower elongated beam, the rigid upper elongated beam and the rigid lower elongated beam are spaced from each other and the rigid proximal forearm portion does not surround the forearm; and wherein the rigid upper elongated beam, the rigid lower elongated beam, the rigid distal hand portion, and the rigid proximal forearm portion are formed as a single unitary structure.

13. The custom brace of claim 12 wherein an edge of the brace body is adapted to be adjacent to a palmar digital crease of the hand.

14. The custom brace of claim 12 wherein the brace body is adapted to not extend over proximal phalanx segments of the fingers.

15. The custom brace of claim 12 wherein the interior surface of the brace has a convex surface that is adapted to be adjacent to a palmar surface of the hand.

16. The custom brace of claim 12 wherein the brace is adapted to prevent palmar flexion movement of the hand.

17. The custom brace of claim 12 wherein the brace is adapted to allow rotational movement of the hand about a center axis of the brace relative to the forearm.

18. The custom brace of claim 12 wherein the distal hand portion is adapted to be adjacent to a palmar surface of the hand.

19. The custom brace of claim 12 wherein the brace body is 3D printed as a single piece structure.

* * * * *